(12) United States Patent
Cheng et al.

(10) Patent No.: US 12,262,712 B2
(45) Date of Patent: Apr. 1, 2025

(54) OXIME ETHER COMPOUND AND APPLICATION THEREOF

(71) Applicants: SHENYANG SINOCHEM AGROCHEMICALS R&D CO., LTD., Liaoning (CN); JIANGSU YANGNONG CHEMICAL CO., LTD., Jiangsu (CN)

(72) Inventors: Xueming Cheng, Liaoning (CN); Haibo Yu, Liaoning (CN); Liang Chen, Liaoning (CN); Hongfei Wu, Liaoning (CN); Geng Sun, Liaoning (CN); Chunxiao Guo, Liaoning (CN); Libao Xu, Liaoning (CN); Jingbo Xu, Liaoning (CN); Ningning Sun, Liaoning (CN)

(73) Assignees: SHENYANG SINOCHEM AGROCHEMICALS R & D CO., LTD., Liaoning (CN); JIANGSU YANGNONG CHEMICAL CO., LTD., Jiangsu (CN)

( * ) Notice: Subject to any disclaimer, the term of this patent is extended or adjusted under 35 U.S.C. 154(b) by 445 days.

(21) Appl. No.: 17/755,625

(22) PCT Filed: Nov. 2, 2020

(86) PCT No.: PCT/CN2020/125780
§ 371 (c)(1),
(2) Date: May 3, 2022

(87) PCT Pub. No.: WO2021/088756
PCT Pub. Date: May 14, 2021

(65) Prior Publication Data
US 2022/0400678 A1  Dec. 22, 2022

(30) Foreign Application Priority Data
Nov. 4, 2019 (CN) .......... 201911065469.2

(51) Int. Cl.
| | |
|---|---|
| A01N 43/78 | (2006.01) |
| A01P 1/00 | (2006.01) |
| A01P 3/00 | (2006.01) |
| C07D 277/40 | (2006.01) |
| C07D 277/46 | (2006.01) |
| C07D 277/50 | (2006.01) |

(52) U.S. Cl.
CPC .............. *A01N 43/78* (2013.01); *A01P 1/00* (2021.08); *A01P 3/00* (2021.08); *C07D 277/40* (2013.01); *C07D 277/46* (2013.01); *C07D 277/50* (2013.01)

(58) Field of Classification Search
CPC .......... A61N 43/78; A01P 3/00; C07D 277/40
See application file for complete search history.

(56) References Cited

U.S. PATENT DOCUMENTS

| | | |
|---|---|---|
| 2013/0096098 A1 | 4/2013 | Gerasimchuk et al. |
| 2016/0002217 A1 | 1/2016 | Rebstock et al. |

FOREIGN PATENT DOCUMENTS

| | | |
|---|---|---|
| CN | 101885708 A | 11/2010 |
| CN | 103804321 A | 5/2014 |
| CN | 106916084 A | 7/2017 |
| CN | 110713443 A | 1/2020 |
| WO | 2008139481 A2 | 11/2008 |

OTHER PUBLICATIONS

Fathalla, Magda Fouad et al.; "Spectrophotometric Determination of pKa's of 1-Hydroxybenzotriazole and Oxime Derivatives in 95% Acetonitrile-Water"; Journal of the Chemical Society of Pakistan, vol. 33, No. 3, 2011; pp. 324-332.

Russell, Stephanie et al.; "Hit-to-Lead Optimization of a Novel Class of Potent, Broad-Spectrum Trypanosomacides"; Journal of Medicinal Chemistry, vol. 59, No. 21, 2016; pp. 9686-9720.

P.J. Keane, Book Review of "A Manual of Assessment Keys for Plant Disease"; Soil Biol. Biochem vol. 13, p. 559.

*Primary Examiner* — Kamal A Saeed
(74) *Attorney, Agent, or Firm* — NKL Law; Allen Xue

(57) ABSTRACT

The present invention discloses an oxime ether compound with novel structure. The structure is shown in general formula I. The definition of each substituent in the formula is provided in the description.

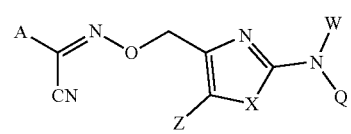

The compound of general formula I has excellent microbicidal 1 activity, and has good control effects on plant bacterial diseases and fungal diseases. The present invention comprises an application of the compound of the general formula I as a microbicide in agriculture and other fields.

9 Claims, No Drawings

OXIME ETHER COMPOUND AND APPLICATION THEREOF

TECHNICAL FIELD

The present invention belongs to the field of fungicide and bactericide in agriculture, and particularly relates to an oxime ether compound and an application thereof.

BACKGROUND

Oxime ether derivatives are a class of compounds with broad-spectrum biological activity and are widely used in agricultural chemicals such as pesticides, herbicides and fungicides. Since the advent of the first commercial oxime ether fungicide, cymoxan, developed by DuPont in the United States in 1974, new commercial varieties have appeared continuously.

Patent CN106916084A discloses the following compounds CK1, CK2 and CK3 (the compound numbers: 107, 115 and 116 in Table 1 of CN106916084A) which have good activity against bacterial and fungal diseases.

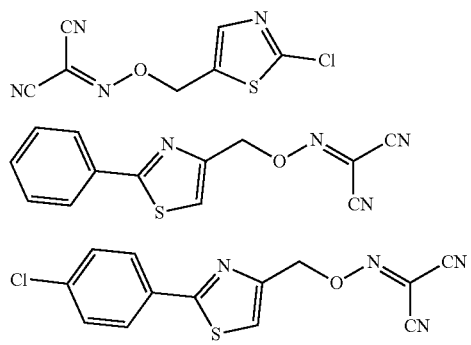

In the prior art, an oxime ether compound shown in the present invention and the bactericidal activity thereof are not reported.

SUMMARY

The purpose of the present invention is to provide a kind of novel oxime ether compounds, which can be used to control disease in agriculture and other fields.

To achieve the above purpose, the present invention adopts the following technical solution:

An oxime ether compound, characterized in that: the compound is shown in general formula I:

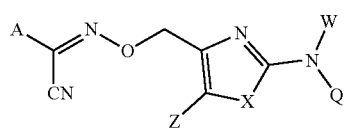

in the formula:
X is selected from sulfur or oxygen;
Z is selected from hydrogen, and $C_1$-$C_6$ linear or branched alkyl unsubstituted or substituted by any of the following groups: halogen, cyano, trifluoromethyl, trifluoromethoxy, hydroxy, nitro and amino;
A is selected from CN, (C=O)O$R^1$, (C=O)NH$R^2$ or (C=O)NHNH$_2$;
$R^1$ is selected from $C_1$-$C_8$ alkyl;
$R^2$ is selected from hydrogen or $C_1$-$C_8$ alkyl;
W is selected from hydrogen, acetonitrile, $C_1$-$C_8$ alkyl, $C_1$-$C_8$ haloalkyl, $C_3$-$C_6$ cycloalkyl, $C_2$-$C_8$ alkenyl, $C_2$-$C_8$ haloalkenyl, $C_2$-$C_8$ alkynyl, $C_2$-$C_8$ haloalkynyl, $C_1$-$C_8$ alkoxy $C_1$-$C_8$ alkyl, C(=O)$R^3$, C(=O)CH$_2R^3$, C(=O)CH$_2$O$R^3$, NO$_2$, O$R^4$, S(O)$_2R^5$, N($R^6$)$R^7$ or N=C($R^8$)$R^9$;
Q is selected from hydrogen, acetonitrile, $C_1$-$C_8$ alkyl, $C_1$-$C_8$ haloalkyl, $C_3$-$C_6$ cycloalkyl, $C_2$-$C_8$ alkenyl, $C_2$-$C_8$ haloalkenyl, $C_2$-$C_8$ alkynyl, $C_2$-$C_8$ haloalkynyl, $C_1$-$C_8$ alkoxy $C_1$-$C_8$ alkyl or C(=O)$R^3$;
or, Q, N and W connected to N form a 3-6 membered saturated or unsaturated ring; the saturated or unsaturated ring contains 0-2 heteroatoms selected from N—$R^{10}$, O, S or oxidized S; and the ring can also be substituted by $R^{11}$ or forms a fused ring with benzene ring;
$R^3$ is selected from hydrogen, $C_1$-$C_8$ alkyl, $C_1$-$C_8$ haloalkyl, $C_3$-$C_6$ cycloalkyl, $C_2$-$C_8$ alkenyl, $C_2$-$C_8$ haloalkenyl, $C_2$-$C_8$ alkynyl, $C_2$-$C_8$ haloalkynyl, $C_1$-$C_8$ alkoxy $C_1$-$C_8$ alkyl, N($R^{12}$)$R^{13}$, optionally substituted aryl or optionally substituted heteroaryl;
$R^4$ is selected from hydrogen, $C_1$-$C_8$ alkyl, $C_1$-$C_8$ haloalkyl or $C_3$-$C_6$ cycloalkyl;
$R^5$ is selected from $C_1$-$C_2$ alkyl, $C_1$-$C_2$ haloalkyl, $C_3$-$C_6$ cycloalkyl, $C_1$-$C_4$ alkoxy, $C_1$-$C_4$ alkyl substituted phenyl or N($R^{12}$)$R^{13}$;
$R^6$ is selected from hydrogen or $C_1$-$C_8$ alkyl;
$R^7$ is selected from hydrogen or $C_1$-$C_8$ alkyl;
$R^8$ is selected from hydrogen, $C_1$-$C_8$ alkyl, $C_1$-$C_8$ haloalkyl, and phenyl unsubstituted or optionally substituted by the following groups, wherein the following groups are hydrogen, halogen, cyano, nitro, $C_1$-$C_4$ alkyl or $C_1$-$C_4$ haloalkyl;
$R^9$ is selected from $C_1$-$C_8$ alkyl, $C_1$-$C_8$ haloalkyl, phenyl unsubstituted or optionally substituted by the following groups, wherein the following groups are hydrogen, halogen, cyano, nitro, $C_1$-$C_4$ alkyl or $C_1$-$C_4$ haloalkyl;
$R^{10}$ is selected from hydrogen, $C_1$-$C_2$ alkyl, $C_1$-$C_2$ haloalkyl, $C_1$-$C_2$ alkylcarbonyl or $C_1$-$C_2$ alkoxycarbonyl;
$R^{11}$ is selected from H, halogen, CN, NO$_2$, $C_1$-$C_2$ alkyl, $C_1$-$C_2$ haloalkyl, $C_1$-$C_4$ alkoxy, $C_1$-$C_2$ haloalkoxy, optionally substituted aryl or S(O)n$R^{14}$, wherein n is 0, 1 or 2;
$R^{12}$ is selected from $C_1$-$C_8$ alkyl;
$R^{13}$ is selected from $C_1$-$C_8$ alkyl;
$R^{14}$ is selected from hydrogen, $C_1$-$C_2$ alkyl, $C_1$-$C_2$ haloalkyl, $C_3$-$C_6$ cycloalkyl or $C_1$-$C_4$ alkoxy;
or a salt of a compound of general formula I.

An optional compound in the present invention is: in the general formula I:
X is selected from sulfur or oxygen;
Z is selected from hydrogen, and $C_1$-$C_3$ linear or branched alkyl unsubstituted or substituted by any of the following groups: halogen, cyano, trifluoromethyl, trifluoromethoxy, hydroxy, nitro and amino;
A is selected from CN, (C=O)O$R^1$, (C=O)NH$R^2$ or (C=O)NHNH$_2$;
$R^1$ is selected from $C_1$-$C_4$ alkyl;
$R^2$ is selected from hydrogen or $C_1$-$C_4$ alkyl;
W is selected from hydrogen, acetonitrile, $C_1$-$C_4$ alkyl, $C_1$-$C_4$ haloalkyl, $C_3$-$C_6$ cycloalkyl, $C_2$-$C_4$ alkenyl, $C_2$-$C_4$ haloalkenyl, $C_2$-$C_4$ alkynyl, $C_2$-$C_4$ haloalkynyl, $C_1$-$C_4$ alkoxy $C_1$-$C_4$ alkyl, $C(=O)R^3$, $C(=O)CH_2R^3$, $C(=O)CH_2OR^3$, $NO_2$, $OR^4$, $S(O)_2R^5$, $N(R^6)R^7$ or $N=C(R^8)R^9$;

Q is selected from hydrogen, acetonitrile, $C_1$-$C_4$ alkyl, $C_1$-$C_4$ haloalkyl, $C_3$-$C_6$ cycloalkyl, $C_2$-$C_4$ alkenyl, $C_2$-$C_4$ haloalkenyl, $C_2$-$C_4$ alkynyl, $C_2$-$C_4$ haloalkynyl, $C_1$-$C_4$ alkoxy $C_1$-$C_4$ alkyl or $C(=O)R^3$;

or, Q, N and W connected to N form a 3-6 membered saturated or unsaturated ring; the saturated or unsaturated ring contains 0-2 N—$R^{10}$, O, S or oxidized S; and the ring can also be substituted by $R^{11}$ or forms a fused ring with benzene ring;

$R^3$ is selected from hydrogen, $C_1$-$C_4$ alkyl, $C_1$-$C_4$ haloalkyl, $C_3$-$C_6$ cycloalkyl, $C_2$-$C_4$ alkenyl, $C_2$-$C_4$ haloalkenyl, $C_2$-$C_4$ alkynyl, $C_2$-$C_4$ haloalkynyl, $C_1$-$C_4$ alkoxy $C_1$-$C_4$ alkyl, $N(R^{12})R^{13}$, non-substituted or substituted phenyl, non-substituted or substituted pyridyl, non-substituted or substituted pyrazolyl, non-substituted or substituted thiazolyl, non-substituted or substituted isothiazolyl or non-substituted or substituted thiadiazolyl, wherein substituent group is selected from the group consisting of hydrogen, halogen, cyano, nitro, hydroxyl, sulfhydryl, amino, aldehyde, $C(=O)NH_2$, $C_1$-$C_4$ alkyl, $C_1$-$C_4$ haloalkyl, $C_3$-$C_6$ cycloalkyl, $C_1$-$C_3$ alkoxy, $C_1$-$C_3$ haloalkoxy, $C_1$-$C_3$ alkylthio, $C_1$-$C_3$ haloalkylthio, $C_1$-$C_3$ alkylamino, $C_1$-$C_3$ dialkylamino, $C_3$-$C_6$ cycloalkylamino, $C_1$-$C_3$ alkoxycarbonyl, $C_1$-$C_3$ alkyl sulfonyl, $C_1$-$C_3$ alkylaminocarbonyl, $C_1$-$C_3$ alkylaminosulfonyl, and non-substituted or substituted phenyl or non-substituted or substituted pyridyl, wherein substituent group is selected from the group consisting of hydrogen, halogen, cyano, nitro, $C_1$-$C_4$ alkyl or $C_1$-$C_4$ haloalkyl;

$R^4$ is selected from hydrogen, $C_1$-$C_4$ alkyl, $C_1$-$C_4$ haloalkyl and $C_3$-$C_6$ cycloalkyl;

$R^5$ is selected from $C_1$-$C_2$ alkyl, $C_1$-$C_2$ haloalkyl, $C_3$-$C_6$ cycloalkyl, $C_1$-$C_4$ alkoxy, $C_1$-$C_4$ alkyl substituted phenyl or $N(R^{12})R^{13}$;

$R^6$ is selected from hydrogen or $C_1$-$C_4$ alkyl;

$R^7$ is selected from hydrogen or $C_1$-$C_4$ alkyl;

$R^8$ is selected from hydrogen, $C_1$-$C_4$ alkyl, $C_1$-$C_4$ haloalkyl, and phenyl unsubstituted or optionally substituted by the following groups, wherein the following groups are hydrogen, halogen, cyano and nitro;

$R^9$ is selected from $C_1$-$C_4$ alkyl, $C_1$-$C_4$ haloalkyl, and phenyl unsubstituted or optionally substituted by the following groups, wherein the following groups are hydrogen, halogen, cyano and nitro;

$R^{10}$ is selected from hydrogen, $C_1$-$C_2$ alkyl, $C_1$-$C_2$ haloalkyl, $C_1$-$C_2$ alkylcarbonyl or $C_1$-$C_2$ alkoxycarbonyl;

$R^{11}$ is selected from H, halogen, CN, $NO_2$, $C_1$-$C_2$ alkyl, $C_1$-$C_2$ haloalkyl, $C_1$-$C_4$ alkoxy, $C_1$-$C_2$ haloalkoxy, optionally substituted aryl or $S(O)_nR^{14}$, wherein n is 0, 1 or 2;

$R^{12}$ is selected from $C_1$-$C_4$ alkyl;

$R^{13}$ is selected from $C_1$-$C_4$ alkyl;

$R^{14}$ is selected from hydrogen, $C_1$-$C_2$ alkyl, $C_1$-$C_2$ haloalkyl, $C_3$-$C_6$ cycloalkyl or $C_1$-$C_4$ alkoxy;

or a salt of a compound of general formula I.

A further optional compound in the present invention is: in the general formula I X is selected from oxygen or sulfur;

Z is selected from hydrogen, methyl or ethyl;

A is selected from CN, $(C=O)OR^1$, $(C=O)NHR^2$ or $(C=O)NHNH_2$;

$R^1$ is selected from methyl or ethyl;

$R^2$ is selected from hydrogen, methyl or ethyl;

W is selected from hydrogen, $C_1$-$C_4$ alkyl, $C_1$-$C_4$ haloalkyl, $C_3$-$C_6$ cycloalkyl, $C(=O)R^3$, $OR^4$, $S(O)_2R^5$, $N(R^6)R^7$ or $N=C(R^8)R^9$;

Q is selected from hydrogen, $C_1$-$C_4$ alkyl, $C_1$-$C_4$ haloalkyl, $C_3$-$C_6$ cycloalkyl or $C(=O)R^3$;

or, Q, N and W connected to N form a 3-6 membered saturated or unsaturated ring; the saturated or unsaturated ring contains 0-2 heteroatoms selected from N—$R^{10}$, O, S or oxidized S; and the ring can also form a fused ring with the benzene ring;

$R^3$ is selected from $C_1$-$C_4$ alkyl, $C_1$-$C_4$ haloalkyl, $C_3$-$C_6$ cycloalkyl, $N(R^{12})R^{13}$, non-substituted or substituted phenyl, non-substituted or substituted pyridyl, non-substituted or substituted pyrazolyl, non-substituted or substituted thiazolyl, non-substituted or substituted isothiazolyl and non-substituted or substituted thiadiazolyl, wherein substituent group is selected from the group consisting of hydrogen, halogen, cyano, nitro, $C(=O)NH_2$, $C_1$-$C_4$ alkyl, $C_1$-$C_4$ haloalkyl, $C_3$-$C_6$ cycloalkyl, $C_1$-$C_3$ alkoxy, $C_1$-$C_3$ haloalkoxy, $C_1$-$C_3$ alkylthio, $C_1$-$C_3$ haloalkylthio, $C_1$-$C_3$ alkylamino, $C_1$-$C_3$ dialkylamino, $C_3$-$C_6$ cycloalkylamino, $C_1$-$C_3$ alkoxycarbonyl, $C_1$-$C_3$ alkylsulfonyl, $C_1$-$C_3$ alkylaminocarbonyl, $C_1$-$C_3$ alkylaminosulfonyl, non-substituted or substituted phenyl and non-substituted or substituted pyridyl, wherein substituent group is selected from the group consisting of hydrogen, halogen, cyano, nitro, $C_1$-$C_4$ alkyl or $C_1$-$C_4$ haloalkyl;

$R^4$ is selected from hydrogen, $C_1$-$C_4$ alkyl or $C_1$-$C_4$ haloalkyl;

$R^5$ is selected from $C_1$-$C_2$ alkyl, $C_1$-$C_2$ haloalkyl, methyl substituted phenyl or $N(R^{11})R^{12}$;

$R^6$ is selected from hydrogen, methyl or ethyl;

$R^7$ is selected from hydrogen, methyl or ethyl;

$R^8$ is selected from methyl, ethyl, trifluoromethyl, and phenyl unsubstituted or optionally substituted by the following groups: the following groups are hydrogen, halogen, cyano and nitro;

$R^9$ is selected from methyl, ethyl, trifluoromethyl, and phenyl unsubstituted or optionally substituted by the following groups: the following groups are hydrogen, halogen, cyano and nitro;

$R^{12}$ is selected from methyl or ethyl;

$R^{13}$ is selected from methyl or ethyl;

or a salt of a compound of general formula I.

A further optional compound in the present invention is: in the general formula I X is selected from oxygen or sulfur;

Z is selected from hydrogen;

A is selected from CN, $(C=O)OR^1$ or $(C=O)NH_2$;

$R^1$ is selected from methyl or ethyl;

W is selected from hydrogen, $C_1$-$C_4$ alkyl, $C_1$-$C_4$ haloalkyl, $C_3$-$C_6$ cycloalkyl, $C(=O)R^3$, $S(O)_2R^5$, $N(R^6)R^7$ or $N=C(R^8)R^9$;

Q is selected from hydrogen, $C_1$-$C_4$ alkyl, $C_1$-$C_4$ haloalkyl, $C_3$-$C_6$ cycloalkyl or $C(=O)R^3$;

$R^3$ is selected from $C_1$-$C_4$ alkyl, $C_1$-$C_4$ haloalkyl, $C_3$-$C_6$ cycloalkyl, $N(R^{12})R^{13}$, non-substituted or substituted phenyl, non-substituted or substituted pyridyl, non-substituted or substituted pyrazolyl, non-substituted or substituted thiazolyl, non-substituted or substituted isothiazolyl and non-substituted or substituted thiadiazolyl, wherein substituent group is selected from the group consisting of hydrogen, halogen, cyano, nitro, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio or $C_1$-$C_4$ haloalkylthio;

$R^5$ is selected from $C_1$-$C_2$ alkyl, $C_1$-$C_2$ haloalkyl, p-methylphenyl or $N(R^{12})R^{13}$;

$R^6$ is selected from hydrogen, methyl or ethyl;
$R^7$ is selected from hydrogen, methyl or ethyl;
$R^8$ is selected from methyl, ethyl, trifluoromethyl, and phenyl unsubstituted or optionally substituted by the following groups: the following groups are hydrogen, halogen, cyano and nitro;
$R^9$ is selected from methyl, ethyl, trifluoromethyl, and phenyl unsubstituted or optionally substituted by the following groups: the following groups are hydrogen, halogen, cyano and nitro;
$R^{12}$ is selected from methyl or ethyl;
$R^{13}$ is selected from methyl or ethyl;
or a salt of a compound of general formula I.

A more further optional compound in the present invention is: in the general formula I
X is selected from sulfur;
Z is selected from hydrogen;
A is selected from CN or (C=O)NH$_2$;
W is selected from hydrogen, $C_1$-$C_4$ alkyl, $C_3$-$C_6$ cycloalkyl, C(=O)R$^3$ or N=C(R$^8$)R$^9$;
Q is selected from hydrogen, $C_1$-$C_4$ alkyl, $C_3$-$C_6$ cycloalkyl or C(=O)R$^3$;
$R^3$ is selected from $C_1$-$C_4$ alkyl, $C_1$-$C_4$ haloalkyl, $C_3$-$C_6$ cycloalkyl, non-substituted or substituted phenyl, non-substituted or substituted pyridyl, non-substituted or substituted pyrazolyl, non-substituted or substituted thiazolyl, non-substituted or substituted isothiazolyl and non-substituted or substituted thiadiazolyl, wherein substituent group is selected from the group consisting of hydrogen, halogen, cyano, nitro, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio or $C_1$-$C_4$ haloalkylthio;
$R^8$ is selected from methyl, ethyl, trifluoromethyl, and phenyl unsubstituted or optionally substituted by the following groups: the following groups are hydrogen, halogen, cyano and nitro;
$R^9$ is selected from methyl, ethyl, trifluoromethyl, and phenyl unsubstituted or optionally substituted by the following groups: the following groups are hydrogen, halogen, cyano and nitro;
or a salt of a compound of general formula I.

A further optional compound in the present invention is: in the general formula I
X is selected from sulfur;
Z is selected from hydrogen;
A is selected from CN or (C=O)NH$_2$;
W is selected from hydrogen, $C_1$-$C_4$ alkyl or C(=O)R$^3$;
Q is selected from hydrogen, $C_1$-$C_4$ alkyl or C(=O)R$^3$;
$R^3$ is selected from $C_1$-$C_4$ alkyl, $C_1$-$C_4$ haloalkyl, $C_3$-$C_6$ cycloalkyl, any group represented by K$^1$-K$^{10}$, non-substituted or substituted phenyl and non-substituted or substituted pyridyl, wherein substituent group is selected from the group consisting of halogen, cyano, nitro, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio or $C_1$-$C_4$ haloalkylthio;
K$^1$-K$^{10}$ are represented as follows:

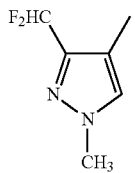

K$^1$

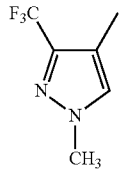

K$^2$

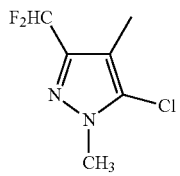

K$^3$

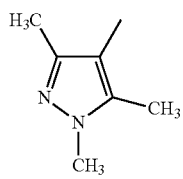

K$^4$

K$^5$

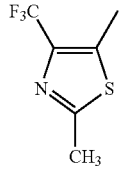

K$^6$

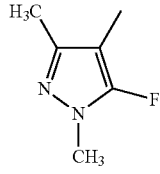

K$^7$

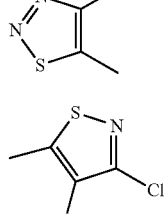

K$^8$

K$^9$

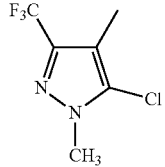

K$^{10}$ or a salt formed by the compound of general formula I and hydrochloric acid, hydrobromic acid, sulfuric acid, phosphoric acid, formic acid, acetic acid, propionic acid, butyric acid, pentanoic acid, trifluoroacetic acid, oxalic acid, malonic acid, methanesulfonic acid, 4-toluenesulfonic acid, malic acid, fumaric acid, lactic acid, maleic acid, salicylic acid, tartaric acid or citric acid.

In the definitions of the compounds of the general formulas provided above, the terms used in the collection generally represent the following substituents:

Unsubstituted means that all substituents are hydrogens.
Halogen: fluorine, chlorine, bromine or iodine.
Alkyl: linear or branched alkyl, such as methyl, ethyl, n-propyl, isopropyl or different butyl, pentyl or hexyl isomers.
Haloalkyl: linear or branched alkyl on which hydrogen atoms can be partially or fully replaced by the halogens, such as chloromethyl, dichloromethyl, trichloromethyl, fluoromethyl, difluoromethyl, trifluoromethyl and heptafluoroisopropyl.
Cycloalkyl: substituted or unsubstituted cyclic alkyl, such as cyclopropyl, cyclopentyl or cyclohexyl. Substituents such as methyl and halogen.
Alkenyl: including linear or branched alkene, such as vinyl, 1-propenyl, 2-propenyl and different butenyl, pentenyl and hexenyl isomers. The alkenyl also comprises polyenes, such as 1,2-propadienyl and 2,4-hexadienyl.
Haloalkenyl: alkenyl in which at least one or more hydrogen atoms can be substituted by a halogen atom.
Alkynyl: including linear or branched alkyne, such as ethynyl, 1-propynyl and different butynyl, pentynyl and hexynyl isomers. The alkynyl also comprises a group consisting of multiple triple bonds, such as 2,5-hexadiynyl.
Haloalkynyl: alkynyl in which at least one or more hydrogen atoms can be substituted by a halogen atom.
Alkoxy: linear or branched alkyl, bonded to the structure through an oxygen atom, such as methoxy, ethoxy and tert-butoxy.
Haloalkoxyalkyl: linear or branched alkoxyalkyl on which hydrogens can be partially or fully replaced by halogen atoms, such as chloromethoxy, dichloromethoxy, trichloromethoxy, fluoromethoxy, difluoromethoxy, trifluoromethoxy, chlorofluoromethoxy and trifluoroethoxy.
Alkylthio: linear or branched alkyl, bonded to the structure through a sulfur atom, such as methylthio and ethylthio.
Haloalkylthio: linear or branched alkylthio on which hydrogen atoms can be partially or fully replaced by the halogens, such as difluoromethylthio and trifluoroethylthio.

Alkylamino: linear or branched alkyl, bonded to the structure through a nitrogen atom, such as methylamino, ethylamino, n-propylamino, isopropylamino or isomeric butylamine.
Dialkylamino: Two identical or different linear or branched alkyls bonded to the structure through nitrogen atoms, such as dimethylamino and methylethylamino.
Cycloalkylamino: cycloalkyl-NH—, such as cyclopropylamino.
Alkylaminocarbonyl: alkyl-NH—CO—, such as $CH_3NHCO$—.
Alkylaminosulfonyl: alkyl-NH—S(O)$_2$—, such as $CH_3NH\ S(O)_2$—.
Alkoxyalkyl: alkyl-O-alkyl-, such as $CH_3OCH_2$—.
Haloalkoxyalkyl: linear or branched alkoxyalkyls on which hydrogen atoms can be partially or fully substituted by the halogens, such as chloromethoxymethyl, dichloromethoxymethyl, trichloromethoxymethyl, fluoromethoxymethyl, difluoromethoxymethyl, trifluoromethoxymethyl, chlorofluoromethoxymethyl and trifluoroethoxymethyl.
Alkoxyalkoxy: alkyl-O-alkyl-O—, such as $CH_3OCH_2O$—.
Oxycarbonyl: alkyl-O—(C=O)—, such as $CH_3O(C=O)$—.
Alkylsulfonyl: alkyl-S(O)$_2$—, such as methyl sulfonyl.
Aryl: monocyclic or polycyclic aromatic group having 6 to 20 carbon atoms, such as phenyl and naphthyl.
Heteroaryl: monocyclic or polycyclic heteraryl group having 1-20 carbon atoms and 1-4 heteroatoms selected from N, S and O, such as pyrrolyl, furyl, thienyl, imidazolyl, pyrazolyl, oxazolyl, thiazolyl, isoxazolyl, isothiazolyl, pyridyl, pyrimidinyl, pyridazinyl, pyridazinone, indoly, benzofuranyl, benzoxazolyl, benzothienyl, benzothiazolyl, benzoisoxazolyl, benzoisothiazolyl, benzimidazolyl, benzopyrazolyl and quinoxalyl.
$C_1$-$C_4$ alkyl substituted phenyl: phenyl may be substituted by 1-5 different or identical $C_1$-$C_4$ alkyls, such as 4-methylphenyl and 2-methyl-3-ethyl phenyl.
Any substituted aryl: aryl at any position may be substituted by any substituent.
Any substituted $C_1$-$C_6$ linear or branched alkyl: each C atom on a linear or branched alkyl of $C_1$-$C_6$ may be substituted by any substituent.
Part of compounds in the formula I in the present invention are shown in Table 1, but the present invention is not limited to the compounds.

TABLE 1

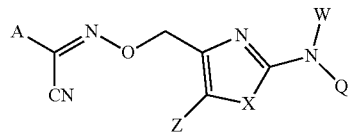

I

| | A | Z | X | W | Q |
|---|---|---|---|---|---|
| 1 | CN | H | S | 4-CF$_3$S—Ph—C(=O)— | H |
| 2 | CN | H | S | 2-Cl—Ph—C(=O)— | H |
| 3 | CN | H | S | 3-Cl—Ph—C(=O)— | H |
| 4 | CN | H | S | 4-Cl—Ph—C(=O)— | H |
| 5 | CN | H | S | 2-F—Ph—C(=O)— | H |
| 6 | CN | H | S | 3-F—Ph—C(=O)— | H |
| 7 | CN | H | S | 4-F—Ph—C(=O)— | H |
| 8 | CN | H | S | 2-Br—Ph—C(=O)— | H |
| 9 | CN | H | S | 3-Br—Ph—C(=O)— | H |
| 10 | CN | H | S | 4-Br—Ph—C(=O)— | H |
| 11 | CN | H | S | 2-I—Ph—C(=O)— | H |

TABLE 1-continued

| | A | Z | X | W | Q |
|---|---|---|---|---|---|
| 12 | CN | H | S | 3-I—Ph—C(=O)— | H |
| 13 | CN | H | S | 4-I—Ph—C(=O)— | H |
| 14 | CN | H | S | 2-Me—Ph—C(=O)— | H |
| 15 | CN | H | S | 3-Me—Ph—C(=O)— | H |
| 16 | CN | H | S | 4-Me—Ph—C(=O)— | H |
| 17 | CN | H | S | 2-MeO—Ph—C(=O)— | H |
| 18 | CN | H | S | 3-MeO—Ph—C(=O)— | H |
| 19 | CN | H | S | 4-MeO—Ph—C(=O)— | H |
| 20 | CN | H | S | 2-$CF_3$—Ph—C(=O)— | H |
| 21 | CN | H | S | 3-$CF_3$—Ph—C(=O)— | H |
| 22 | CN | H | S | 4-$CF_3$—Ph—C(=O)— | H |
| 23 | CN | H | S | 2-$CF_3$O—Ph—C(=O)— | H |
| 24 | CN | H | S | 3-$CF_3$O—Ph—C(=O)— | H |
| 25 | CN | H | S | 6-Cl-2-C(=O)—pyridyl | H |
| 26 | CN | H | S | 2-Cl-3-C(=O)—pyridyl | H |
| 27 | CN | H | S | 4-Cl-3-C(=O)—pyridyl | H |
| 28 | CN | H | S | 5-Cl-3-C(=O)—pyridyl | H |
| 29 | CN | H | S | 6-Cl-3-C(=O)—pyridyl | H |
| 30 | CN | H | S | 2-Cl-4-C(=O)—pyridyl | H |
| 31 | CN | H | S | 3-Cl-4-C(=O)—pyridyl | H |
| 32 | CN | H | S | 1-C(=O)—naphthyl | H |
| 33 | CN | H | S | 2-C(=O)—naphthyl | H |
| 34 | CN | H | S | 2,4-diCl—Ph—C(=O)— | H |
| 35 | CN | H | S | 2,6-diCl—Ph—C(=O)— | H |
| 36 | CN | H | S | 3,4-diCl—Ph—C(=O)— | H |
| 37 | CN | H | S | 3,5-diCl—Ph—C(=O)— | H |
| 38 | CN | H | S | 2-Cl-6-F—Ph—C(=O)— | H |
| 39 | CN | H | S | 2-Cl-4-Me—Ph—C(=O)— | H |
| 40 | CN | H | S | 2,4-di(MeO)—Ph—C(=O)— | H |
| 41 | CN | H | S | 2-Cl-4-Et—Ph—C(=O)— | H |
| 42 | CN | H | S | 2-Cl-5-$NO_2$—Ph—C(=O)— | H |
| 43 | CN | H | S | 3-Cl-4-Me—Ph—C(=O)— | H |
| 44 | CN | H | S | 4-Cl-3-Me—Ph—C(=O)— | H |
| 45 | CN | H | S | 3-F-4-$NO_2$—Ph—C(=O)— | H |
| 46 | CN | H | S | 2,3,4,5,6-5F—Ph—C(=O)— | H |
| 47 | CN | H | S | H | H |
| 48 | CN | H | S | 4-$CF_3$O—Ph—C(=O)— | H |
| 49 | CN | H | S | 2-$CHF_2$O—Ph—C(=O)— | H |
| 50 | CN | H | S | 3-$CHF_2$O—Ph—C(=O)— | H |
| 51 | CN | H | S | 4-$CHF_2$O—Ph—C(=O)— | H |
| 52 | CN | H | S | 2-$(CF_3)_2$CF—Ph—C(=O)— | H |
| 53 | CN | H | S | 3-$(CF_3)_2$CF—Ph—C(=O)— | H |
| 54 | CN | H | S | 4-$(CF_3)_2$CF—Ph—C(=O)— | H |
| 55 | CN | H | S | 2-$NO_2$—Ph—C(=O)— | H |
| 56 | CN | H | S | 3-$NO_2$—Ph—C(=O)— | H |
| 57 | CN | H | S | 4-$NO_2$—Ph—C(=O)— | H |
| 58 | CN | H | S | 2-CN—Ph—C(=O)— | H |
| 59 | CN | H | S | 3-CN—Ph—C(=O)— | H |
| 60 | CN | H | S | 4-CN—Ph—C(=O)— | H |
| 61 | CN | H | S | 2-$N(CH_3)_2$—Ph—C(=O)— | H |
| 62 | CN | H | S | 3-$N(CH_3)_2$—Ph—C(=O)— | H |
| 63 | CN | H | S | 4-$N(CH_3)_2$—Ph—C(=O)— | H |
| 64 | CN | H | S | 2-C(=O)-pyridyl | H |
| 65 | CN | H | S | 3-C(=O)-pyridyl | H |
| 66 | CN | H | S | 4-C(=O)-pyridyl | H |
| 67 | CN | H | S | 2-C(=O)-furyl | H |
| 68 | CN | H | S | 2-C(=O)-thiazolyl | H |
| 69 | CN | H | S | 3-Cl-2-C(=O)-thiazolyl | H |
| 70 | CN | H | S | 4-Cl-2-C(=O)-pyridyl | H |
| 71 | CN | H | S | 5-Cl-2-C(=O)-pyridyl | H |
| 72 | CN | H | S | 4-CF3-3-C(=O)-pyridyl | H |
| 73 | CN | H | S | 2-F-4-CN—Ph—C(=O)— | H |
| 74 | CN | H | S | 3-CF3-4-F—Ph—C(=O)— | H |
| 75 | CN | H | S | 2,4-diMe—Ph—C(=O)— | H |
| 76 | CN | H | S | 2,5-diMe—Ph—C(=O)— | H |
| 77 | CN | H | S | 3,4-diMe—Ph—C(=O)— | H |
| 78 | CN | H | S | 3,4-di(MeO)—Ph—C(=O)— | H |
| 79 | CN | H | S | 3,5-di(MeO)—Ph—C(=O)— | H |
| 80 | CN | H | S | 3,5-di(CF3)—Ph—C(=O)— | H |
| 81 | CN | H | S | 2,5-diCl-4-F—Ph—C(=O)— | H |

TABLE 1-continued
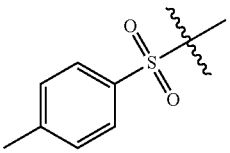 [SMILES: *S(=O)(=O)c1ccc(C)cc1]
I
| | A | Z | X | W | Q |
|---|---|---|---|---|---|
| 82 | CN | H | S | 2,4,5-triCl—Ph—C(=O)— | H |
| 83 | CN | H | S | 2,4,6-triCl—Ph—C(=O)— | H |
| 84 | CN | H | S | 2,4,6-triCH$_3$—Ph—C(=O)— | H |
| 85 | CN | H | S | 2-F-4-CN—Ph—C(=O)— | H |
| 86 | CN | H | S | 2,4-diF—Ph—C(=O)— | H |
| 87 | CN | H | S | 3,4-diF—Ph—C(=O)— | H |
| 88 | CN | H | S | 3,5-diF—Ph—C(=O)— | H |
| 89 | CN | H | S | 2,6-diF—Ph—C(=O)— | H |
| 90 | CN | H | S | 2,4,5-triF—Ph—C(=O)— | H |
| 91 | CN | H | S | 3,4,5-triF—Ph—C(=O)— | H |
| 92 | CN | H | S | 2,4,6-triF—Ph—C(=O)— | H |
| 93 | CN | H | S | 2-C(=O)-quinoline | H |
| 94 | CN | H | S | 6-C(=O)-quinoline | H |
| 95 | CN | H | S | Ph—C(=O)— | H |
| 96 | CN | H | S | 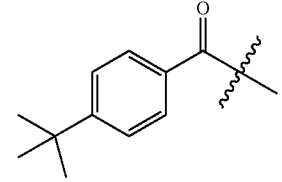 [SMILES: *C(=O)c1ccc(C(C)(C)C)cc1] | H |
| 97 | CN | H | S | 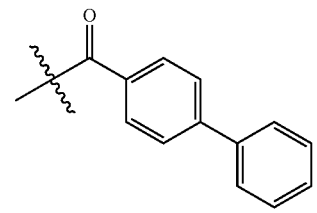 [SMILES: *C(=O)c1ccc(-c2ccccc2)cc1] | H |
| 98 | CN | H | S | 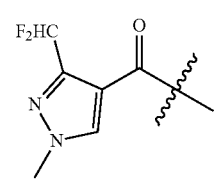 [SMILES: *C(=O)c1cn(C)nc1C(F)F] | H |
| 99 | CN | H | S | 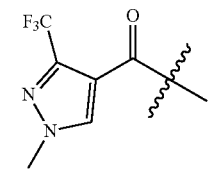 [SMILES: *C(=O)c1cn(C)nc1C(F)(F)F] | H |
| 100 | CN | H | S |  | H |

TABLE 1-continued
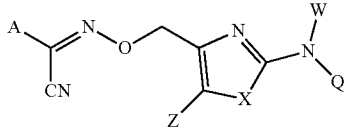
| | A | Z | X | W | Q |
|---|---|---|---|---|---|
| 101 | CN | H | S | 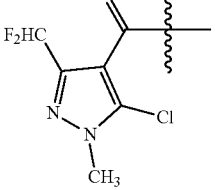 | H |
| 102 | CN | H | S | 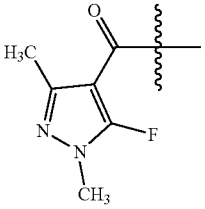 [SMILES: *C(=O)c1c(C)nn(C)c1F] | H |
| 103 | CN | H | S | 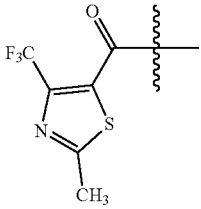 [SMILES: *C(=O)c1sc(C)nc1C(F)(F)F] | H |
| 104 | CN | H | S | 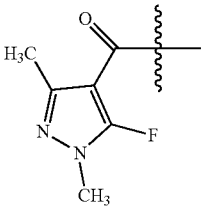 [SMILES: *C(=O)c1c(C)nn(C)c1F] | H |
| 105 | CN | H | S | 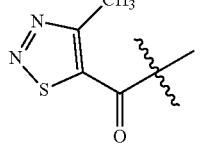 | H |
| 106 | CN | H | S | 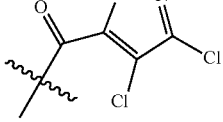 | H |
| 107 | CN | H | S |  | H |

TABLE 1-continued
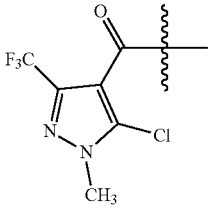
I
|     | A  | Z   | X | W | Q |
|-----|-----|-----|---|---|---|
| 108 | CN | H | S | 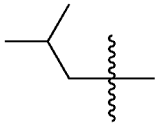 [SMILES: *CC(C)C] | H |
| 109 | CN | H | S | 4-CF₃—Ph—C(=O)— | CH₃ |
| 110 | CN | H | S | 4-Br—Ph—C(=O)— | CH₃ |
| 111 | CN | H | S | Ph—C(=O)— | CH₃ |
| 112 | CN | H | S | Ph—C(=O)— | CH₃CH₂ |
| 113 | CN | H | S | 4-Cl—Ph—C(=O)— | CH₃CH₂CH₂ |
| 114 | CN | H | S | 4-Cl—Ph—C(=O)— | 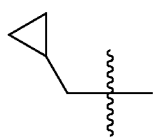 [SMILES: *CC1CC1] |
| 115 | CN | H | S | 4-F—Ph—C(=O)— | 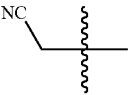 |
| 116 | CN | H | S | 4-F—Ph—C(=O)— | 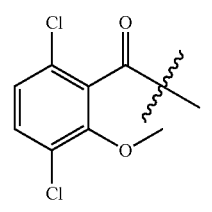 [SMILES: *C(=O)c1c(Cl)ccc(Cl)c1OC] |
| 117 | CN | H | S | CH₃—CH=CH—C(=O)— | H |
| 118 | CN | H | S | CH₃CH₂—C(=O)— | H |
| 119 | CN | H | S | CF₃—C(=O)— | H |
| 120 | CN | H | S | CF₃CF₂—C(=O)— | H |
| 121 | CN | H | S | CF₃CH₂—C(=O)— | H |
| 122 | CN | H | S | (CH₃)₃C—C(=O)— | H |
| 123 | CN | H | S | (CH₃)₃C—O—C(=O)— | H |
| 124 | CN | H | S | Cl—CH₂—C(=O)— | H |
| 125 | CN | H | O | H | H |
| 126 | CN | CH₃ | S | H | H |
| 127 | CN | CF3 | S | H | H |
| 128 | CN | H | S | 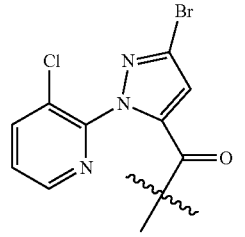 [SMILES: *C(=O)c1cc(Br)nn1-c1ncccc1Cl] | H |
| 129 | CN | H | S |  | H |

TABLE 1-continued

Structure I: A-C(CN)=N-O-CH2-[thiazole ring with Z at 5-position, X at position, linked to N(W)(Q)]

| | A | Z | X | W | Q |
|---|---|---|---|---|---|
| 130 | CN | H | S | (phenylacetyl; PhCH2C(=O)—) | H |
| 131 | CN | H | S | (4-Cl-phenylacetyl; 4-Cl-PhCH2C(=O)—) | H |
| 132 | CN | H | S | (4-Cl-phenoxyacetyl; 4-Cl-Ph-O-CH2-C(=O)—) | H |
| 133 | (C=O)NH2 | H | S | 4-CF3S—Ph—C(=O)— | H |
| 134 | (C=O)NH2 | H | S | 2-Cl—Ph—C(=O)— | H |
| 135 | (C=O)NH2 | H | S | 3-Cl—Ph—C(=O)— | H |
| 136 | (C=O)NH2 | H | S | 4-Cl—Ph—C(=O)— | H |
| 137 | (C=O)NH2 | H | S | 2-F—Ph—C(=O)— | H |
| 138 | (C=O)NH2 | H | S | 3-F—Ph—C(=O)— | H |
| 139 | (C=O)NH2 | H | S | 4-F—Ph—C(=O)— | H |
| 140 | (C=O)NH2 | H | S | 2-Br—Ph—C(=O)— | H |
| 141 | (C=O)NH2 | H | S | 3-Br—Ph—C(=O)— | H |
| 142 | (C=O)NH2 | H | S | 4-Br—Ph—C(=O)— | H |
| 143 | (C=O)NH2 | H | S | 2-I—Ph—C(=O)— | H |
| 144 | (C=O)NH2 | H | S | 3-I—Ph—C(=O)— | H |
| 145 | (C=O)NH2 | H | S | 4-I—Ph—C(=O)— | H |
| 146 | (C=O)NH2 | H | S | 2-Me—Ph—C(=O)— | H |
| 147 | (C=O)NH2 | H | S | 3-Me—Ph—C(=O)— | H |
| 148 | (C=O)NH2 | H | S | 4-Me—Ph—C(=O)— | H |
| 149 | (C=O)NH2 | H | S | 2-MeO—Ph—C(=O)— | H |
| 150 | (C=O)NH2 | H | S | 3-MeO—Ph—C(=O)— | H |
| 151 | (C=O)NH2 | H | S | 4-MeO—Ph—C(=O)— | H |
| 152 | (C=O)NH2 | H | S | 2-CF3—Ph—C(=O)— | H |
| 153 | (C=O)NH2 | H | S | 3-CF3—Ph—C(=O)— | H |
| 154 | (C=O)NH2 | H | S | 4-CF3—Ph—C(=O)— | H |
| 155 | (C=O)NH2 | H | S | 2-CF3O—Ph—C(=O)— | H |
| 156 | (C=O)NH2 | H | S | 3-CF3O—Ph—C(=O)— | H |
| 157 | (C=O)NH2 | H | S | 6-Cl-2-C(=O)-pyridyl | H |
| 158 | (C=O)NH2 | H | S | 2-Cl-3-C(=O)-pyridyl | H |
| 159 | (C=O)NH2 | H | S | 4-Cl-3-C(=O)-pyridyl | H |
| 160 | (C=O)NH2 | H | S | 5-Cl-3-C(=O)-pyridyl | H |
| 161 | (C=O)NH2 | H | S | 6-Cl-3-C(=O)-pyridyl | H |
| 162 | (C=O)NH2 | H | S | 2-Cl-4-C(=O)-pyridyl | H |
| 163 | (C=O)NH2 | H | S | 3-Cl-4-C(=O)-pyridyl | H |
| 164 | (C=O)NH2 | H | S | 1-C(=O)-naphthyl | H |
| 165 | (C=O)NH2 | H | S | 2-C(=O)-naphthyl | H |
| 166 | (C=O)NH2 | H | S | 2,4-diCl—Ph—C(=O)— | H |
| 167 | (C=O)NH2 | H | S | 2,6-diCl—Ph—C(=O)— | H |
| 168 | (C=O)NH2 | H | S | 3,4-diCl—Ph—C(=O)— | H |
| 169 | (C=O)NH2 | H | S | 3,5-diCl—Ph—C(=O)— | H |
| 170 | (C=O)NH2 | H | S | 2-Cl-6-F—Ph—C(=O)— | H |
| 171 | (C=O)NH2 | H | S | 2-Cl-4-Me—Ph-C(=O)— | H |
| 172 | (C=O)NH2 | H | S | 2,4-di(MeO)—Ph—C(=O)— | H |
| 173 | (C=O)NH2 | H | S | 2-Cl-4-Et—Ph—C(=O)— | H |
| 174 | (C=O)NH2 | H | S | 2-Cl-5-NO2—Ph—C(=O)— | H |
| 175 | (C=O)NH2 | H | S | 3-Cl-4-Me—Ph—C(=O)— | H |
| 176 | (C=O)NH2 | H | S | 4-Cl-3-Me—Ph—C(=O)— | H |
| 177 | (C=O)NH2 | H | S | 2-F-4-Me—Ph—C(=O)— | H |
| 178 | (C=O)NH2 | H | S | 2,3,4,5,6-5F—Ph—C(=O)— | H |
| 179 | (C=O)NH2 | H | S | H | H |

TABLE 1-continued

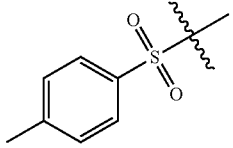 [SMILES: *S(=O)(=O)c1ccc(C)cc1]

| | A | Z | X | W | Q |
|---|---|---|---|---|---|
| 180 | (C=O)NH$_2$ | H | S | 4-CF$_3$O—Ph—C(=O)— | H |
| 181 | (C=O)NH$_2$ | H | S | 2-CHF$_2$O—Ph—C(=O)— | H |
| 182 | (C=O)NH$_2$ | H | S | 3-CHF$_2$O—Ph—C(=O)— | H |
| 183 | (C=O)NH$_2$ | H | S | 4-CHF$_2$O—Ph—C(=O)— | H |
| 184 | (C=O)NH$_2$ | H | S | 2-(CF$_3$)$_2$CF—Ph—C(=O)— | H |
| 185 | (C=O)NH$_2$ | H | S | 3-(CF$_3$)$_2$CF—Ph—C(=O)— | H |
| 186 | (C=O)NH$_2$ | H | S | 4-(CF$_3$)$_2$CF—Ph—C(=O)— | H |
| 187 | (C=O)NH$_2$ | H | S | 2-NO$_2$—Ph—C(=O)— | H |
| 188 | (C=O)NH$_2$ | H | S | 3-NO$_2$—Ph—C(=O)— | H |
| 189 | (C=O)NH$_2$ | H | S | 4-NO$_2$—Ph—C(=O)— | H |
| 190 | (C=O)NH$_2$ | H | S | 2-CN—Ph—C(=O)— | H |
| 191 | (C=O)NH$_2$ | H | S | 3-CN—Ph—C(=O)— | H |
| 192 | (C=O)NH$_2$ | H | S | 4-CN—Ph—C(=O)— | H |
| 193 | (C=O)NH$_2$ | H | S | 2-N(CH$_3$)$_2$—Ph—C(=O)— | H |
| 194 | (C=O)NH$_2$ | H | S | 3-N(CH$_3$)$_2$—Ph—C(=O)— | H |
| 195 | (C=O)NH$_2$ | H | S | 4-N(CH$_3$)$_2$—Ph—C(=O)— | H |
| 196 | (C=O)NH$_2$ | H | S | 2-C(=O)-pyridyl | H |
| 197 | (C=O)NH$_2$ | H | S | 3-C(=O)-pyridyl | H |
| 198 | (C=O)NH$_2$ | H | S | 4-C(=O)-pyridyl | H |
| 199 | (C=O)NH$_2$ | H | S | 2-C(=O)-furyl | H |
| 200 | (C=O)NH$_2$ | H | S | 2-C(=O)-thiazolyl | H |
| 201 | (C=O)NH$_2$ | H | S | 3-Cl-2-C(=O)-thiazolyl | H |
| 202 | (C=O)NH$_2$ | H | S | 4-Cl-2-C(=O)-pyridyl | H |
| 203 | (C=O)NH$_2$ | H | S | 5-Cl-2-C(=O)-pyridyl | H |
| 204 | (C=O)NH$_2$ | H | S | 4-CF3-3-C(=O)-pyridyl | H |
| 205 | (C=O)NH$_2$ | H | S | 2-F-4-CN—Ph—C(=O)— | H |
| 206 | (C=O)NH$_2$ | H | S | 3-F-4-Me—Ph—C(=O)— | H |
| 207 | (C=O)NH$_2$ | H | S | 2,4-diMe—Ph—C(=O)— | H |
| 208 | (C=O)NH$_2$ | H | S | 2,5-diMe—Ph—C(=O)— | H |
| 209 | (C=O)NH$_2$ | H | S | 3,4-diMe—Ph—C(=O)— | H |
| 210 | (C=O)NH$_2$ | H | S | 3,4-di(MeO)—Ph—C(=O)— | H |
| 211 | (C=O)NH$_2$ | H | S | 3,5-di(MeO)—Ph—C(=O)— | H |
| 212 | (C=O)NH$_2$ | H | S | 3,5-di(CF$_3$)—Ph—C(=O)— | H |
| 213 | (C=O)NH$_2$ | H | S | 2,5-diCl-4-F—Ph—C(=O)— | H |
| 214 | (C=O)NH$_2$ | H | S | 2,4,5-triCl—Ph—C(=O)— | H |
| 215 | (C=O)NH$_2$ | H | S | 2,4,6-triCl—Ph—C(=O)— | H |
| 216 | (C=O)NH$_2$ | H | S | 2,4,6-triCH$_3$—Ph—C(=O)— | H |
| 217 | (C=O)NH$_2$ | H | S | 2-F-4-CN—Ph—C(=O)— | H |
| 218 | (C=O)NH$_2$ | H | S | 2,4-diF—Ph—C(=O)— | H |
| 219 | (C=O)NH$_2$ | H | S | 3,4-diF—Ph—C(=O)— | H |
| 220 | (C=O)NH$_2$ | H | S | 3,5-diF—Ph—C(=O)— | H |
| 221 | (C=O)NH$_2$ | H | S | 2,6-diF—Ph—C(=O)— | H |
| 222 | (C=O)NH$_2$ | H | S | 2,4,5-triF—Ph—C(=O)— | H |
| 223 | (C=O)NH$_2$ | H | S | 3,4,5-triF—Ph—C(=O)— | H |
| 224 | (C=O)NH$_2$ | H | S | 2,4,6-triF—Ph—C(=O)— | H |
| 225 | (C=O)NH$_2$ | H | S | 2-C(=O)-quinoline | H |
| 226 | (C=O)NH$_2$ | H | S | 6-C(=O)-quinoline | H |
| 227 | (C=O)NH$_2$ | H | S | Ph—C(=O)— | H |
| 228 | (C=O)NH$_2$ | H | S | 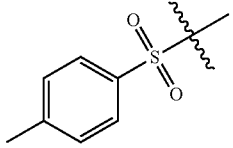 [SMILES: *S(=O)(=O)c1ccc(C)cc1] | H |
| 229 | (C=O)NH$_2$ | H | S | 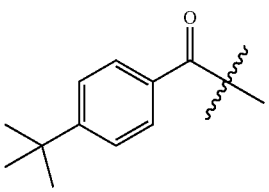 [SMILES: *C(=O)c1ccc(C(C)(C)C)cc1] | H |

TABLE 1-continued

| | A | Z | X | W | Q |
|---|---|---|---|---|---|
| 230 | (C=O)NH₂ | H | S | 3-biphenylcarbonyl | H |
| 231 | (C=O)NH₂ | H | S | 3-(difluoromethyl)-1-methyl-1H-pyrazol-4-yl carbonyl | H |
| 232 | (C=O)NH₂ | H | S | 1-methyl-3-(trifluoromethyl)-1H-pyrazol-4-yl carbonyl | H |
| 233 | (C=O)NH₂ | H | S | 5-chloro-3-(difluoromethyl)-1-methyl-1H-pyrazol-4-yl carbonyl | H |
| 234 | (C=O)NH₂ | H | S | 1,3,5-trimethyl-1H-pyrazol-4-yl carbonyl | H |
| 235 | (C=O)NH₂ | H | S | 5-fluoro-1,3-dimethyl-1H-pyrazol-4-yl carbonyl | H |
| 236 | (C=O)NH₂ | H | S | 2-methyl-4-(trifluoromethyl)thiazol-5-yl carbonyl | H |

TABLE 1-continued

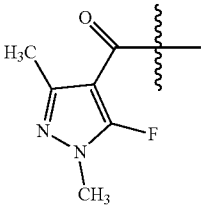 [SMILES: *C(=O)c1c(C)nn(C)c1F]

I

|  | A | Z | X | W | Q |
|---|---|---|---|---|---|
| 237 | (C=O)NH₂ | H | S | 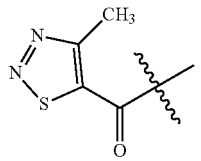 [SMILES: *C(=O)c1snnc1C] | H |
| 238 | (C=O)NH₂ | H | S |  | H |
| 239 | (C=O)NH₂ | H | S | 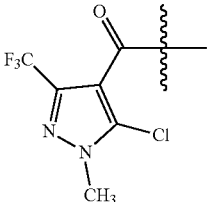 | H |
| 240 | (C=O)NH₂ | H | S | 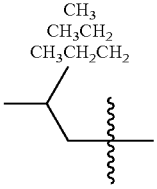 | H |
| 241 | (C=O)NH₂ | H | S | Ph—C(=O)— | CH₃ |
| 242 | (C=O)NH₂ | H | S | Ph—C(=O)— | CH₃CH₂ |
| 243 | (C=O)NH₂ | H | S | 4-Cl—Ph—C(=O)— | CH₃CH₂CH₂ |
| 244 | (C=O)NH₂ | H | S | 4-Cl—Ph—C(=O)— | 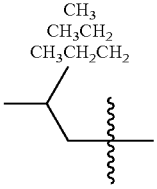 |
| 245 | (C=O)NH₂ | H | S | 4-F—Ph—C(=O)— | 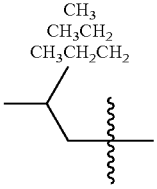 |
| 246 | (C=O)NH₂ | H | S | 4-F—Ph—C(=O)— | 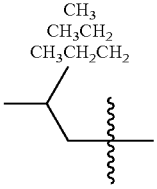 |
| 247 | (C=O)NH₂ | H | S | CH₃—C(=O)— | H |
| 248 | (C=O)NH₂ | H | S | CH₃CH₂—C(=O)— | H |
| 249 | (C=O)NH₂ | H | S | CF₃—C(=O)— | H |
| 250 | (C=O)NH₂ | H | S | CF₃CF₂—C(=O)— | H |
| 251 | (C=O)NH₂ | H | S | CF₃CH₂—C(=O)— | H |
| 252 | (C=O)NH₂ | H | S | (CH₃)₃C—C(=O)— | H |
| 253 | (C=O)NH₂ | H | S | (CH₃)₃C—O—C(=O)— | H |
| 254 | (C=O)NH₂ | H | S | Cl—CH₂—C(=O)— | H |
| 255 | (C=O)NH₂ | H | O | H | H |

TABLE 1-continued

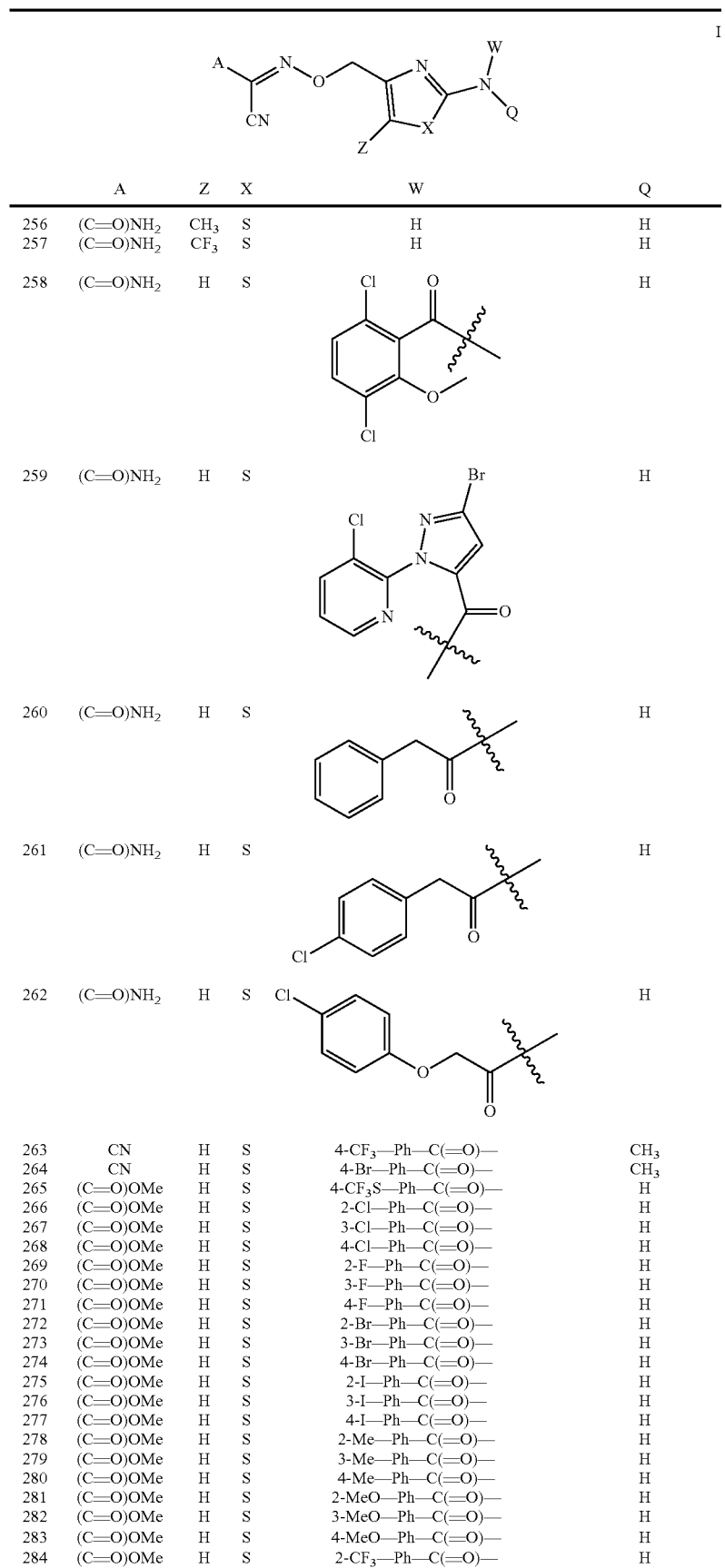

| | A | Z | X | W | Q |
|---|---|---|---|---|---|
| 256 | (C=O)NH₂ | CH₃ | S | H | H |
| 257 | (C=O)NH₂ | CF₃ | S | H | H |
| 258 | (C=O)NH₂ | H | S | 2,6-diCl-3-MeO-Ph-C(=O)- | H |
| 259 | (C=O)NH₂ | H | S | [3-Br-1-(3-Cl-pyridin-2-yl)pyrazol-5-yl]-C(=O)- | H |
| 260 | (C=O)NH₂ | H | S | Ph-CH₂-C(=O)- | H |
| 261 | (C=O)NH₂ | H | S | 4-Cl-Ph-CH₂-C(=O)- | H |
| 262 | (C=O)NH₂ | H | S | 4-Cl-Ph-O-CH₂-C(=O)- | H |
| 263 | CN | H | S | 4-CF₃-Ph-C(=O)- | CH₃ |
| 264 | CN | H | S | 4-Br-Ph-C(=O)- | CH₃ |
| 265 | (C=O)OMe | H | S | 4-CF₃S-Ph-C(=O)- | H |
| 266 | (C=O)OMe | H | S | 2-Cl-Ph-C(=O)- | H |
| 267 | (C=O)OMe | H | S | 3-Cl-Ph-C(=O)- | H |
| 268 | (C=O)OMe | H | S | 4-Cl-Ph-C(=O)- | H |
| 269 | (C=O)OMe | H | S | 2-F-Ph-C(=O)- | H |
| 270 | (C=O)OMe | H | S | 3-F-Ph-C(=O)- | H |
| 271 | (C=O)OMe | H | S | 4-F-Ph-C(=O)- | H |
| 272 | (C=O)OMe | H | S | 2-Br-Ph-C(=O)- | H |
| 273 | (C=O)OMe | H | S | 3-Br-Ph-C(=O)- | H |
| 274 | (C=O)OMe | H | S | 4-Br-Ph-C(=O)- | H |
| 275 | (C=O)OMe | H | S | 2-I-Ph-C(=O)- | H |
| 276 | (C=O)OMe | H | S | 3-I-Ph-C(=O)- | H |
| 277 | (C=O)OMe | H | S | 4-I-Ph-C(=O)- | H |
| 278 | (C=O)OMe | H | S | 2-Me-Ph-C(=O)- | H |
| 279 | (C=O)OMe | H | S | 3-Me-Ph-C(=O)- | H |
| 280 | (C=O)OMe | H | S | 4-Me-Ph-C(=O)- | H |
| 281 | (C=O)OMe | H | S | 2-MeO-Ph-C(=O)- | H |
| 282 | (C=O)OMe | H | S | 3-MeO-Ph-C(=O)- | H |
| 283 | (C=O)OMe | H | S | 4-MeO-Ph-C(=O)- | H |
| 284 | (C=O)OMe | H | S | 2-CF₃-Ph-C(=O)- | H |

TABLE 1-continued

| | A | Z | X | W | Q |
|---|---|---|---|---|---|
| 285 | (C=O)OMe | H | S | 3-CF₃—Ph—C(=O)— | H |
| 286 | (C=O)OMe | H | S | 4-CF₃—Ph—C(=O)— | H |
| 287 | (C=O)OMe | H | S | 2-CF₃O—Ph—C(=O)— | H |
| 288 | (C=O)OMe | H | S | 3-CF₃O—Ph—C(=O)— | H |
| 289 | (C=O)OMe | H | S | 6-Cl-2-C(=O)-pyridyl | H |
| 290 | (C=O)OMe | H | S | 2-Cl-3-C(=O)-pyridyl | H |
| 291 | (C=O)OMe | H | S | 4-Cl-3-C(=O)-pyridyl | H |
| 292 | (C=O)OMe | H | S | 5-Cl-3-C(=O)-pyridyl | H |
| 293 | (C=O)OMe | H | S | 6-Cl-3-C(=O)-pyridyl | H |
| 294 | (C=O)OMe | H | S | 2-Cl-4-C(=O)-pyridyl | H |
| 295 | (C=O)OMe | H | S | 3-Cl-4-C(=O)-pyridyl | H |
| 296 | (C=O)OMe | H | S | 1-C(=O)-naphthyl | H |
| 297 | (C=O)OMe | H | S | 2-C(=O)-naphthyl | H |
| 298 | (C=O)OMe | H | S | 2,4-diCl—Ph—C(=O)— | H |
| 299 | (C=O)OMe | H | S | 2,6-diCl—Ph—C(=O)— | H |
| 300 | (C=O)OMe | H | S | 3,4-diCl—Ph—C(=O)— | H |
| 301 | (C=O)OMe | H | S | 3,5-diCl—Ph—C(=O)— | H |
| 302 | (C=O)OMe | H | S | 2-Cl-6-F—Ph—C(=O)— | H |
| 303 | (C=O)OMe | H | S | 2-Cl-4-Me—Ph—C(=O)— | H |
| 304 | (C=O)OMe | H | S | 2,4-di(MeO)—Ph—C(=O)— | H |
| 305 | (C=O)OMe | H | S | 2-Cl-4-Et—Ph—C(=O)— | H |
| 306 | (C=O)OMe | H | S | 2-Cl-5-NO₂—Ph—C(=O)— | H |
| 307 | (C=O)OMe | H | S | 3-Cl-4-Me—Ph—C(=O)— | H |
| 308 | (C=O)OMe | H | S | 4-Cl-3-Me—Ph—C(=O)— | H |
| 309 | (C=O)OMe | H | S | 2-F-4-Me—Ph—C(=O)— | H |
| 310 | (C=O)OMe | H | S | 2,3,4,5,6-5F—Ph—C(=O)— | H |
| 311 | (C=O)OMe | H | S | H | H |
| 312 | (C=O)NHMe | H | S | 4-CF₃S—Ph—C(=O)— | H |
| 313 | (C=O)NHMe | H | S | 2-Cl—Ph—C(=O)— | H |
| 314 | (C=O)NHMe | H | S | 3-Cl—Ph—C(=O)— | H |
| 315 | (C=O)NHMe | H | S | 4-Cl—Ph—C(=O)— | H |
| 316 | (C=O)NHMe | H | S | 2-F—Ph—C(=O)— | H |
| 317 | (C=O)NHMe | H | S | 3-F—Ph—C(=O)— | H |
| 318 | (C=O)NHMe | H | S | 4-F—Ph—C(=O)— | H |
| 319 | (C=O)NHMe | H | S | 2-Br—Ph—C(=O)— | H |
| 320 | (C=O)NHMe | H | S | 3-Br—Ph—C(=O)— | H |
| 321 | (C=O)NHMe | H | S | 4-Br—Ph—C(=O)— | H |
| 322 | (C=O)NHMe | H | S | 2-I—Ph—C(=O)— | H |
| 323 | (C=O)NHMe | H | S | 3-I—Ph—C(=O)— | H |
| 324 | (C=O)NHMe | H | S | 4-I—Ph—C(=O)— | H |
| 325 | (C=O)NHMe | H | S | 2-Me—Ph—C(=O)— | H |
| 326 | (C=O)NHMe | H | S | 3-Me—Ph—C(=O)— | H |
| 327 | (C=O)NHMe | H | S | 4-Me—Ph—C(=O)— | H |
| 328 | (C=O)NHMe | H | S | 2-MeO—Ph—C(=O)— | H |
| 329 | (C=O)NHMe | H | S | 3-MeO—Ph—C(=O)— | H |
| 330 | (C=O)NHMe | H | S | 4-MeO—Ph—C(=O)— | H |
| 331 | (C=O)NHMe | H | S | 2-CF₃—Ph—C(=O)— | H |
| 332 | (C=O)NHMe | H | S | 3-CF₃—Ph—C(=O)— | H |
| 333 | (C=O)NHMe | H | S | 4-CF₃—Ph—C(=O)— | H |
| 334 | (C=O)NHMe | H | S | 2-CF₃O—Ph—C(=O)— | H |
| 335 | (C=O)NHMe | H | S | 3-CF₃O—Ph—C(=O)— | H |
| 336 | (C=O)NHMe | H | S | 6-Cl-2-C(=O)-pyridyl | H |
| 337 | (C=O)NHMe | H | S | 2-Cl-3-C(=O)-pyridyl | H |
| 338 | (C=O)NHMe | H | S | 4-Cl-3-C(=O)-pyridyl | H |
| 339 | (C=O)NHMe | H | S | 5-Cl-3-C(=O)-pyridyl | H |
| 340 | (C=O)NHMe | H | S | 6-Cl-3-C(=O)-pyridyl | H |
| 341 | (C=O)NHMe | H | S | 2-Cl-4-C(=O)-pyridyl | H |
| 342 | (C=O)NHMe | H | S | 3-Cl-4-C(=O)-pyridyl | H |
| 343 | (C=O)NHMe | H | S | 1-C(=O)-naphthyl | H |
| 344 | (C=O)NHMe | H | S | 2-C(=O)-naphthyl | H |
| 345 | (C=O)NHMe | H | S | 2,4-diCl—Ph—C(=O)— | H |
| 346 | (C=O)NHMe | H | S | 2,6-diCl—Ph—C(=O)— | H |
| 347 | (C=O)NHMe | H | S | 3,4-diCl—Ph—C(=O)— | H |
| 348 | (C=O)NHMe | H | S | 3,5-diCl—Ph—C(=O)— | H |
| 349 | (C=O)NHMe | H | S | 2-Cl-6-F—Ph—C(=O)— | H |
| 350 | (C=O)NHMe | H | S | 2-Cl-4-Me—Ph—C(=O)— | H |
| 351 | (C=O)NHMe | H | S | 2,4-di(MeO)—Ph—C(=O)— | H |
| 352 | (C=O)NHMe | H | S | 2-Cl-4-Et—Ph—C(=O)— | H |
| 353 | (C=O)NHMe | H | S | 2-Cl-5-NO₂—Ph—C(=O)— | H |
| 354 | (C=O)OEt | H | S | H | H |

TABLE 1-continued
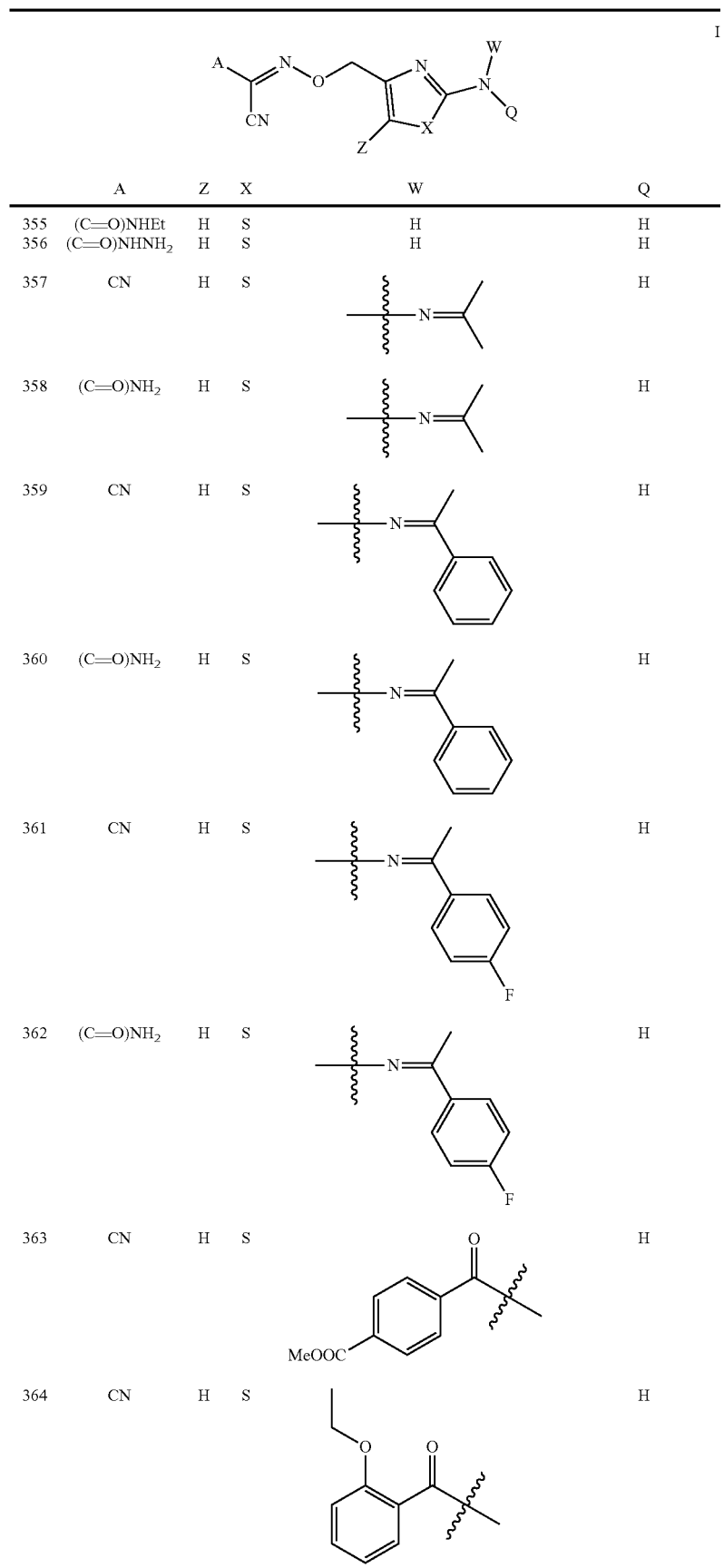
| | A | Z | X | W | Q |
|---|---|---|---|---|---|
| 355 | (C=O)NHEt | H | S | H | H |
| 356 | (C=O)NHNH$_2$ | H | S | H | H |
| 357 | CN | H | S | ![N=C(CH3)2] | H |
| 358 | (C=O)NH$_2$ | H | S | ![N=C(CH3)2] | H |
| 359 | CN | H | S | ![N=C(CH3)(Ph)] | H |
| 360 | (C=O)NH$_2$ | H | S | ![N=C(CH3)(Ph)] | H |
| 361 | CN | H | S | ![N=C(CH3)(4-F-Ph)] | H |
| 362 | (C=O)NH$_2$ | H | S | ![N=C(CH3)(4-F-Ph)] | H |
| 363 | CN | H | S | ![4-MeOOC-Ph-C(=O)-C(CH3)2-] | H |
| 364 | CN | H | S | ![2-EtO-Ph-C(=O)-C(CH3)2-] | H |

TABLE 1-continued

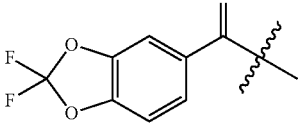

| | A | Z | X | W | Q |
|---|---|---|---|---|---|
| 365 | CN | H | S | 4-Et—Ph—C(=O)— | H |
| 366 | CN | H | S | 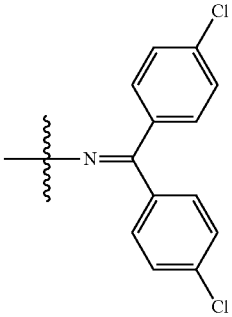 [SMILES: *N=C(c1ccc(Cl)cc1)c1ccc(Cl)cc1] | H |
| 367 | CN | H | S | ![diaryl methylene imine with two 4-Cl-Ph groups] | H |
| 368 | CN | H | S | 2,5-diF—Ph—C(=O)— | H |
| 369 | CN | H | S | 3,5-diMe—Ph—C(=O)— | H |

$^1$H NMR and physicochemical properties of some compounds are as follows:

TABLE 2

| No. | Compound | $^1$H NMR (600 MHz) | Physical Property |
|---|---|---|---|
| 1 | 2 | CDCl$_3$: 7.93-7.91 (m, 1H), 7.51-7.50 (m, 2H), 7.45-7.42 (m, 1H), 7.14 (t, 1H), 5.50 (d, 2H). | yellow solid |
| 2 | 4 | CDCl$_3$: 7.88 (d, 2H), 7.52 (d, 2H), 7.13 (s, 1H), 5.50 (s, 2H). | yellow solid |
| 3 | 5 | CDCl3: 8.21 (td, 1H), 7.61 (dddd, 1H), 7.36 (ddd, 1H), 7.24-7.21 (m, 1H), 7.12 (s, 1H), 5.53 (d, 2H). | yellow solid |
| 4 | 6 | CDCl3: 7.73-7.67 (m, 2H), 7.53 (td, 1H), 7.36-7.31 (m, 1H), 7.14 (s, 1H), 5.52 (d, 2H). | yellow solid |
| 5 | 16 | CDCl$_3$: 7.84 (d, 2H), 7.34 (d, 2H), 7.11 (s, 1H), 5.51 (s, 2H), 2.44 (s, 3H) | red oil |
| 6 | 19 | CDCl$_3$: 7.91 (d, 2H), 7.09 (s, 1H), 7.01 (d, 2H), 5.51 (s, 2H). | yellow solid |
| 7 | 20 | CDCl$_3$: 7.83 (d, 1H), 7.74-7.66 (m, 3H), 7.16 (s, 1H), 5.50 (s, 2H). | yellow oil |
| 8 | 22 | CDCl$_3$: 8.06 (d, 2H), 7.82 (d, 2H), 7.16 (s, 1H), 5.52 (s, 2H). | black oil |
| 9 | 23 | CDCl$_3$: 8.11 (d, 1H), 7.66-7.63 (m, 1H), 7.50-7.47 (m, 1H), 7.41-7.39 (m, 1H), 7.13 (s, 1H), 5.51 (s, 2H). | yellow oil |
| 10 | 34 | CDCl$_3$: 7.91 (d, 1H), 7.54 (d, 1H), 7.45-7.43 (t, 1H), 7.16 (s, 1H), 5.52 (s, 2H). | yellow solid |
| 11 | 36 | CDCl$_3$: 8.05 (d, 1H), 7.75 (dd, 1H), 7.63 (d, 1H), 7.15 (s, 1H), 5.51 (s, 2H). | yellow solid |
| 12 | 45 | CDCl$_3$: 8.28-8.21 (m, 1H), 7.99 (d, 1H), 7.91 (d, 1H), 7.21 (s, 1H), 5.55 (s, 2H). | yellow solid |
| 13 | 47 | CDCl$_3$: 6.65 (s, 1H), 5.37 (s, 2H), 5.11 (s, 2H). | yellow solid |
| 14 | 65 | DMSO-d$_6$: 9.18 (d, 1H), 8.76 (t, H), 8.39 (t, 1H), 7.55 (t, 1H), 7.50 (s, 1H), 5.58 (s, 2H). | yellow solid |
| 15 | 74 | CDCl$_3$: 8.28 (dd, 1H), 8.19 (ddd, 1H), 7.39 (t, 1H), 7.15 (d, 1H), 5.51 (s, 2H). | white solid |
| 16 | 86 | CDCl$_3$: 7.91 (d, 2H), 7.09 (s, 1H), 7.01 (d, 2H), 5.51 (s, 2H). | yellow solid |
| 17 | 87 | CDCl$_3$: 7.84 (dd, 1H), 7.70 (d, 1H), 7.34 (dd, 1H), 7.14 (s, 1H), 5.51 (s, 2H) | yellow solid |
| 18 | 95 | CDCl$_3$: 7.95 (t, 2H), 7.64 (dd, 1H), 7.55 (dd, 2H), 7.13 (s, 1H), 5.51 (s, 2H). | red oil |

TABLE 2-continued

| No. | Compound | $^1$H NMR (600 MHz) | Physical Property |
|---|---|---|---|
| 19 | 97 | CDCl$_3$: 7.93 (d, 2H), 7.57 (d, 2H), 7.12 (s, 1H), 5.54 (s, 2H), 1.37 (s, 9H). | white solid |
| 20 | 99 | CDCl$_3$: 8.35 (s, 1H), 7.09 (s, 1H), 5.96 (t, 1H), 5.51 (s, 2H), 4.02 (s, 3H). | yellow solid |
| 21 | 104 | CDCl$_3$: 7.17 (s, 1H), 5.52 (s, 2H), 2.81 (s, 3H). | yellow solid |
| 22 | 117 | CDCl$_3$: 7.14 (dd, 1H), 7.05 (s, 1H), 5.98 (dq, 1H), 5.49 (t, 2H), 1.97 (dd, 3H). | yellow solid |
| 23 | 118 | CDCl$_3$: 7.05 (s, 1H), 5.48 (s, 1H), 2.51 (dd, 2H), 1.28 (t, 3H). | red solid |
| 24 | 119 | CDCl$_3$: 6.62 (s, 1H), 5.41 (s, 2H). | yellow solid |
| 25 | 123 | CDCl$_3$: 6.99 (s, 1H), 5.48 (d, 2H), 1.54 (s, 9H). | yellow oil |
| 26 | 134 | DMSO-d$_6$: 7.97 (d, 2H), 7.60 (dd, 1H), 7.55 (dd, 1H), 7.51 (td, 1H), 7.44 (d, 1H), 7.42 (dd, 1H), 5.42 (s, 2H). | yellow solid |
| 27 | 179 | DMSO-d$_6$: 7.99 (d, 2H), 7.05 (s, 2H), 6.72 (s, 1H), 5.22 (s, 2H). | yellow solid |
| 28 | 228 | DMSO-d$_6$: 8.02 (d, 2H), 7.73-7.59 (m, 2H), 7.34-7.27 (m, 2H), 7.01 (s, 1H), 5.18 (s, 2H), 2.31 (s, 3H). | yellow solid |
| 29 | 253 | CDCl$_3$: 6.96 (s, 1H), 5.37 (d, 2H), 1.54 (s, 9H). | yellow oil |
| 30 | 361 | CDCl$_3$: 7.75 (dd, 2H), 7.09 (t, 2H), 6.81 (s, 1H), 5.43 (d, 2H), 2.26 (s, 3H). | black oil |
| 31 | 363 | CDCl$_3$: 8.22 (d, 2H), 8.05 (d, 2H), 7.16 (s, 1H), 5.54 (s, 2H), 3.98 (s, 3H). | yellow solid |
| 32 | 364 | CDCl$_3$: 8.30 (d, 1H), 7.56 (t, 1H), 7.16 (t, 1H), 7.08 (s, 1H), 7.07 (d, 1H), 5.54 (s, 2H), 4.37 (dd, 2H), 1.67 (t, 3H). | yellow solid |
| 33 | 365 | CDCl$_3$: 7.85 (d, 2H), 7.36 (d, 3H), 7.11 (s, 1H), 5.50 (s, 2H), 2.73 (q, 2H), 1.27 (t, 3H). | yellow solid |
| 34 | 366 | CDCl$_3$: 7.74-7.22 (m, 2H), 7.20 (d, 1H), 7.13 (s, 1H), 5.49 (s, 2H). | yellow solid |
| 35 | 367 | CDCl$_3$: 7.57 (d, 2H), 7.47 (d, 2H), 7.31 (d, 2H), 7.23 (d, 2H), 6.82 (s, 1H), 5.36 (d, 2H). | black oil |
| 36 | 368 | CDCl$_3$: 7.90 (ddd, 1H), 7.32-7.28 (m, 1H), 7.24-7.21 (m, 1H), 7.15 (s, 1H), 5.53 (d, 2H). | yellow solid |
| 37 | 369 | CDCl$_3$: 7.59-7.51 (m, 2H), 7.11 (s, 1H), 5.51 (s, 2H), 2.39 (d, 6H). | yellow solid |

The compound of the formula I in the present invention can be prepared by the following method. Unless otherwise stated, the definitions of the groups in the formula are the same as above.

Method I:

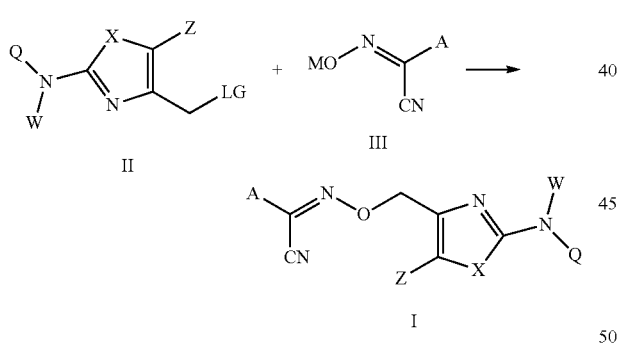

The compound of the formula II and the compound of the formula III react in a suitable solvent at temperature of −10° C. to a boiling point of the solvent for 0.5-48 hours to obtain the compound of the formula I.

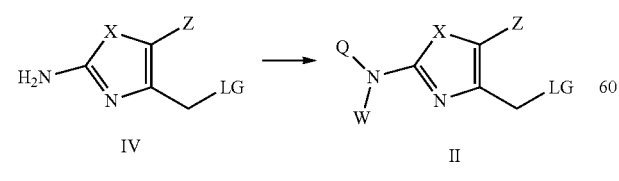

The compound of the formula IV containing amino reacts with W and Q in a suitable solvent at a temperature from −10° C. to the boiling point of the solvent for 0.5-48 hours to obtain the compound of the formula II. The reaction can be carried out in the presence or absence of a base.

Method II:

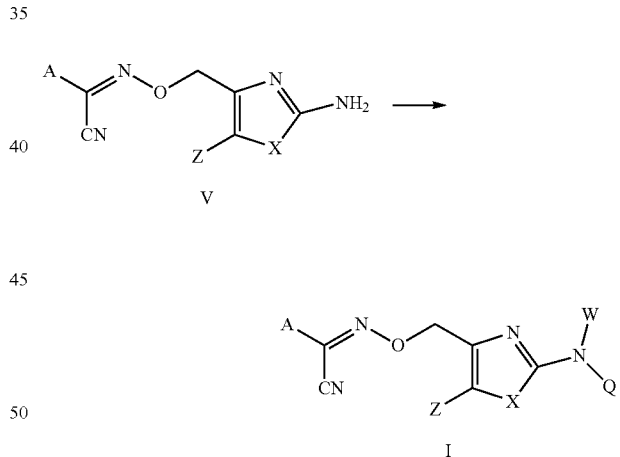

The compound of the formula V containing amino reacts with W and Q in a suitable solvent at a temperature from −10° C. to the boiling point of the solvent for 0.5-48 hours to obtain the compound of the formula I. The reaction can be carried out in the presence or absence of a base.

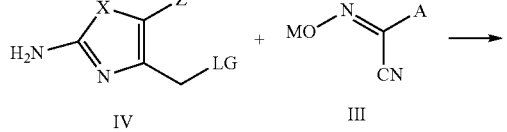

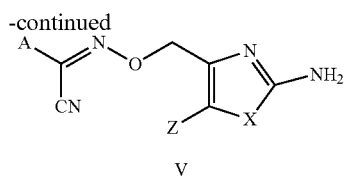

V

The compound of the formula IV and the compound of the formula III react in a suitable solvent at a temperature of −10° C. to a boiling point of the solvent for 0.5-48 hours to obtain the compound of the formula V.

In the above preparation method: LG represents a leaving group, and a suitable leaving group may be selected from a halogen or other conventional freestone groups, such as mesylate or tosylate. M represents a cation, such as Na$^+$, K$^+$, CS$^+$, Ag$^+$ or NH$_4^+$. The suitable solvent may be aromatic hydrocarbons such as benzene, toluene and xylene, ketone such as acetone, methyl ethyl ketone and methyl isobutyl ketone, halogenated aromatic hydrocarbons such as chloroform and dichloromethane, esters such as methyl acetate and ethyl acetate, ethers such as tetrahydrofuran, dioxane, diethyl ether and 1,2-dimethoxyethane, polar solvents such as water, acetonitrile, N,N-dimethylformamide, N-methylpyrrolidone and dimethylsulfoxide, or a mixed solvent of the above solvents. The base can be organic bases such as triethylamine, pyridine, DBU and DMAP, alkali metal hydrides such as sodium hydride and potassium hydride, alkali metal hydroxides such as sodium hydroxide and potassium hydroxide, alkaline earth metal hydroxides such as calcium hydroxide, alkali metal carbonates such as sodium carbonate and potassium carbonate, alkali metal hydrogencarbonates such as sodium bicarbonate, and metal alkoxides such as sodium methoxide and potassium ethoxide.

The compounds of the formula III can be purchased or prepared according to known methods (e.g., CN103804321, WO2008139481, US20130096098 or Journal of the Chemical Society of Pakistan, 33(3), 324-332, 2011, etc.).

The compounds of the formula IV can be purchased or prepared by known methods (e.g., CN 101885708A or Journal of Medicinal Chemistry, 59(21), 9686-9720; 2016).

The compound or the salt of the present invention is used for controlling plant diseases, and can be used for controlling diseases caused by various fungi such as oomycetes, basidiomycetes, ascomycetes and fungi imperfecti on various crops, and for example, a lower dose of the compound has good control effects on cucumber downy mildew, cucumber gray mildew, cucumber anthracnose, cucumber powdery mildew, tomato early blight, tomato late blight, pepper blight, grape downy mildew, grape white rot, apple ring rot, apple spotted leaf disease, rice sheath blight, rice blast, wheat rust, wheat leaf spot, wheat powdery mildew, sclerotinia rot of colza, corn southern leaf blight and other diseases.

The compounds of the present invention also have good bactericidal activity, and can be used to control various plant bacterial diseases, such as bacterial wilt, bacterial blight, canker, soft rot, bacterial angular spot, bacterial stripe, leaf blight, wildfire and bacterial scab, specifically including rice bacterial leaf spot, rice bacterial blight, rice base rot, rice bacterial brown stripe, rice bacterial brown spot, potato bacterial wilt, potato soft rot, potato black shank, potato bacterial ring rot, citrus canker, pear root cancer, pear fire blight, peach bacterial perforation, kiwifruit canker, walnut black spot, fruit tree bacterial root cancer, watermelon bacterial wilt, watermelon bacterial fruit rot, solanaceae vegetable bacterial wilt, *Pseudomonas syringae* pv. *lachrymans*, melon bacterial angular spot, cruciferous vegetable soft rot, bacterial black rot, bacterial black spot and flower bacterial diseases.

The present invention also provides a fungicidal composition. The composition comprises the compound of the formula I or a salt thereof and an agriculturally acceptable carrier; the compound of the formula I or a salt thereof is used as an active ingredient; and the weight percentage of the active ingredient in the composition is 0.1-99%.

DETAILED DESCRIPTION

The following specific embodiments are used to further illustrate the present invention, but are not intended to limit the present invention.

Synthesis Embodiments

Embodiment 1

Preparation of Compound 34

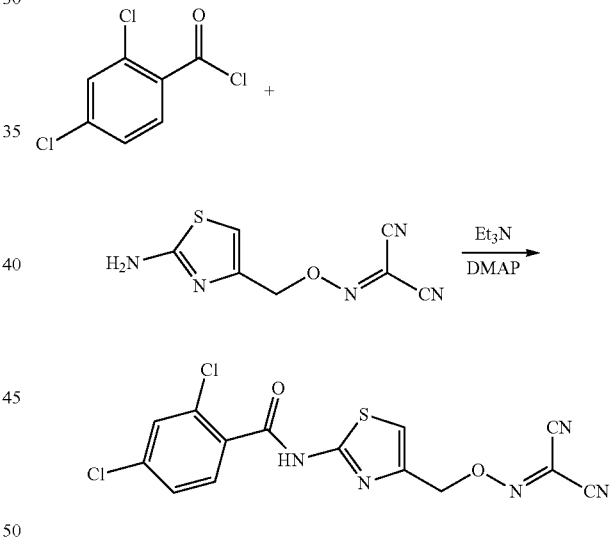

((2-aminothiazole-4-yl)methoxy)iminoimide dicyanide (0.5 g, 2.41 mmol), triethylamine (0.37 g, 3.66 mmol), DMAP (0.3 g, 2.46 mmol) and 20 ml of dichloromethane were added to a 50 ml reaction flask; then stirring was started; then 2.4-dichlorobenzoyl chloride (0.5 g, 2.39 mmol) was dissolved in 10 ml of dichloromethane; an acid chloride solution was added dropwise to the reaction flask under ice bath conditions; after dropping, the reaction was continued while stirring at room temperature; TLC (ethyl acetate:petroleum ether=1:5) monitoring was conducted; after the reaction was completed, the solvent was evaporated under reduced pressure; and the residue was purified by column chromatography (ethyl acetate:petroleum ether=1:5 as eluent; 100-140-mesh silica gel produced by Qingdao Marine Biological Chemical Plant Branch) to obtain 0.42 g of yellow solid, with a yield of 46%.

Embodiment 2

Preparation of Compound 47

Preparation of Intermediate 4-(chloromethyl)thiazole-2-amino hydrochloride

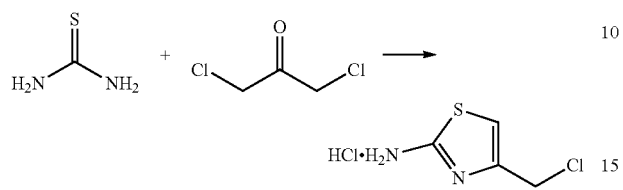

Thiourea (6.49 g, 85.26 mmol) and 40 ml of methanol were added to a 100 ml reaction flask; then 1,3-dichloroacetone (10.83 g, 85.26 mmol) was dissolved in 30 ml of acetone; under ice bath conditions, the 1,3-dichloroacetone solution was slowly added dropwise to the thiourea solution; after dropping, an ice bath was removed and stirring was continued; the solution was stirred overnight at room temperature, and spin-dried to remove the solvent; then 20 ml of acetone was added to the residue, and stirred vigorously until solid was precipitated; and then the solid was subjected to suction filtration and air drying to obtain 13.5 g of white solid, with a yield of 86%.

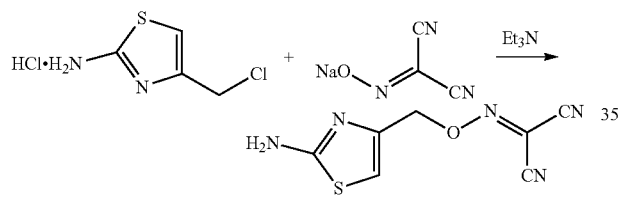

4-(chloromethyl)thiazole-2-amino hydrochloride (0.5 g, 2.7 mmol), sodium malononitrile oxime ether (0.32 g, 2.7 mmol), triethylamine (0.28 g, 2.77 mmol) and 15 ml of acetonitrile were added to a 50 ml reaction flask; the temperature was raised to 60° C. to conduct the reaction while stirring; TLC (ethyl acetate:petroleum ether=1:1) monitoring was conducted; after the reaction was completed, the solvent was evaporated under reduced pressure; and the residue was purified by column chromatography (ethyl acetate:petroleum ether=1:2 as an eluent; 100-140-mesh silica gel produced by Qingdao Marine Biological Chemical Plant Branch) to obtain 0.21 g of yellow solid, with a yield of 37%.

Embodiment 3

Preparation of Compound 97

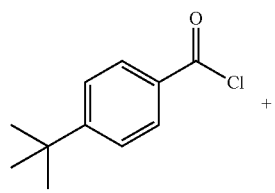

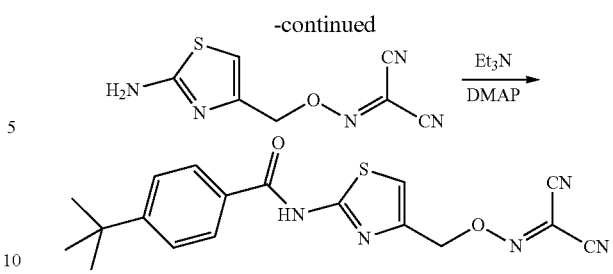

((2-aminothiazole-4-yl)methoxy)iminoimide dicyanide (0.27 g, 1.30 mmol), triethylamine (0.19 g, 1.88 mmol), DMAP (0.16 g, 1.31 mmol) and 20 ml of dichloromethane were added to a 50 ml reaction flask; then stirring was started; then 4-tert-butylbenzoyl chloride (0.25 g, 1.27 mmol) was dissolved in 10 ml of dichloromethane; an acid chloride solution was added dropwise to the reaction flask under ice bath conditions; after dropping, the reaction was continued while stirring at room temperature; TLC (ethyl acetate:petroleum ether=1:5) monitoring was conducted; after the reaction was completed, the solvent was evaporated under reduced pressure; and the residue was purified by column chromatography (ethyl acetate:petroleum ether=1:5 as eluent; 100-140-mesh silica gel produced by Qingdao Marine Biological Chemical Plant Branch) to obtain 0.22 g of black oil, with a yield of 47%.

Embodiment 4

Preparation of Compound 179

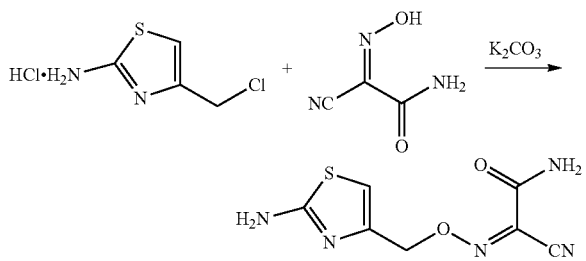

4-(chloromethyl)thiazole-2-amino hydrochloride (0.45 g, 2.43 mmol), cyanoacetamidoxime ether (0.28 g, 2.48 mmol), potassium carbonate (1.01 g, 7.29 mmol) and 25 ml of acetonitrile were added to a 50 ml reaction flask; stirring was conducted at 65° C. for reaction for 8 hours; after cooling, the reaction solution was filtered with diatomite to obtain a clear solution; then, the solvent was removed under reduced pressure; and the residue was washed with dichloromethane to obtain 0.22 g of yellow solid, with a yield of 40%.

Embodiment 5

Preparation of Compound 361

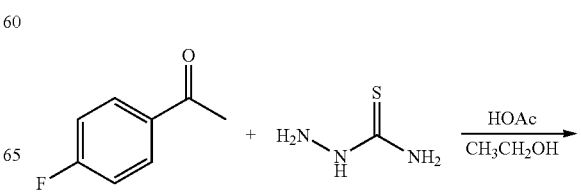

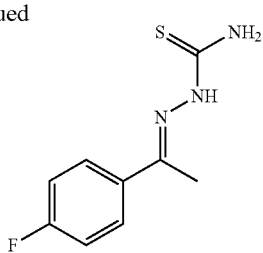

4-fluoroacetophenone (2 g, 14.48 mmol), thiosemicarbazide (1.32 g, 14.48 mmol), 0.2 ml of acetic acid and 35 ml of ethanol were added to a 50 ml reaction flask, and heated to reflux and react for 8 hours; and after the reaction solution was cooled, white solid was precipitated, and then filtered to obtain 2.2 g of target object, with a yield of 72%.

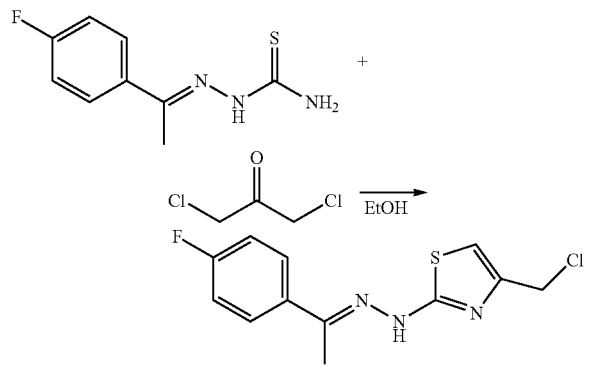

The condensation product (1.2 g, 5.68 mmol) and 1,3-dichloroacetone (0.72 g, 5.68 mmol) obtained in the previous step were added to a single-neck flask; then 50 ml of ethanol was added, and heated to 60° C. to react for 8 hours; TLC (ethyl acetate:petroleum ether=1:5) monitoring was conducted; after the reaction was completed, the solvent was evaporated under reduced pressure; and the residue was purified by column chromatography (ethyl acetate:petroleum ether=1:5 as an eluent; 100-140-mesh silica gel produced by Qingdao Marine Biological Chemical Plant Branch) to obtain 0.66 g of black oil, with a yield of 41%.

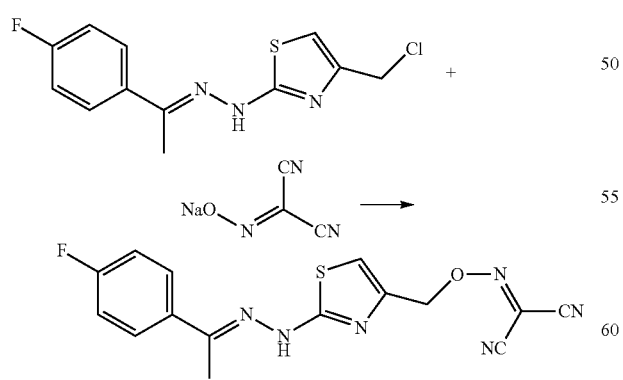

The chloride (0.4 g, 1.41 mmol) obtained in the previous step, sodium malononitrile oxime ether (0.17 g, 1.41 mmol) and 15 ml of acetonitrile were added to a 50 ml reaction flask, and heated to 60° C. to react while stirring; TLC (ethyl acetate:petroleum ether=1:3) monitoring was conducted; after the reaction was completed, the solvent was evaporated off under reduced pressure; and the residue was purified by column chromatography (ethyl acetate:petroleum ether=1:3 as an eluent; 100-140-mesh silica gel produced by Qingdao Marine Biological Chemical Plant Branch) to obtain 0.18 g of black oil, with a yield of 37%.

Embodiment 6

Preparation of Compound 363

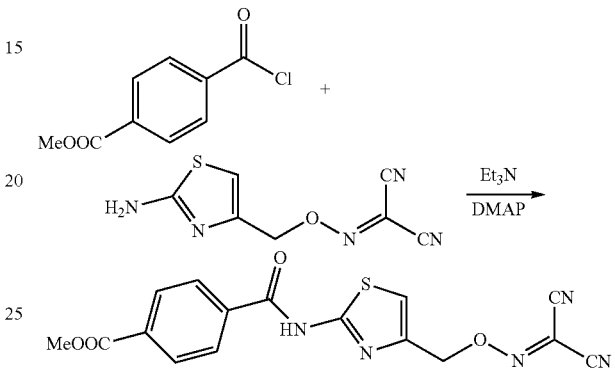

((2-aminothiazole-4-yl)methoxy)iminoimide dicyanide (0.21 g, 1.01 mmol), triethylamine (0.16 g, 1.58 mmol), DMAP (0.13 g, 1.06 mmol) and 20 ml of dichloromethane were added to a 50 ml reaction flask; then stirring was started; then methyl 4-formate benzoyl chloride (0.20 g, 1.01 mmol) was dissolved in 10 ml of dichloromethane; an acid chloride solution was added dropwise to the reaction flask under ice bath conditions; after dropping, the reaction was continued while stirring at room temperature; TLC (ethyl acetate:petroleum ether=1:5) monitoring was conducted; after the reaction was completed, the solvent was evaporated under reduced pressure; and the residue was purified by column chromatography (ethyl acetate:petroleum ether=1:5 as eluent; 100-140-mesh silica gel produced by Qingdao Marine Biological Chemical Plant Branch) to obtain 0.18 g of yellow solid, with a yield of 48%.

Embodiment 7

Preparation of Compound 364

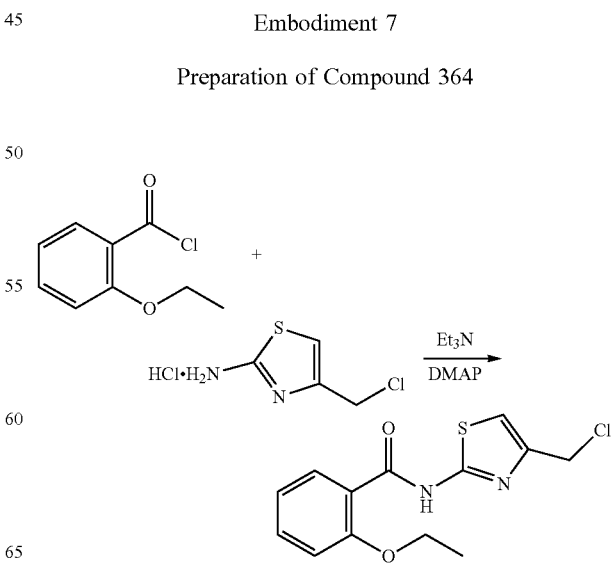

4-(chloromethyl)thiazole-2-amino hydrochloride (0.4 g, 2.16 mmol), triethylamine (0.54 g, 5.34 mmol), DMAP (0.26 g, 2.13 mmol) mol) and 20 ml of dichloromethane were added to a 50 ml reaction flask, and then stirring was started. O-ethoxybenzoyl chloride (0.39 g, 2.11 mmol) was dissolved in 10 ml of dichloromethane; then acid chloride was added dropwise to the reaction flask under ice bath conditions; after dropping, the reaction was continued while stirring at room temperature; TLC (ethyl acetate:petroleum ether=1:5) monitoring was conducted; after the reaction was completed, the solvent was removed under reduced pressure; and the residue was purified by column chromatography (ethyl acetate:petroleum ether=1:5 as an eluent; 100-140-mesh silica gel produced by Qingdao Marine Biological Chemical Plant Branch) to obtain 0.46 g of white solid, with a yield of 73%.

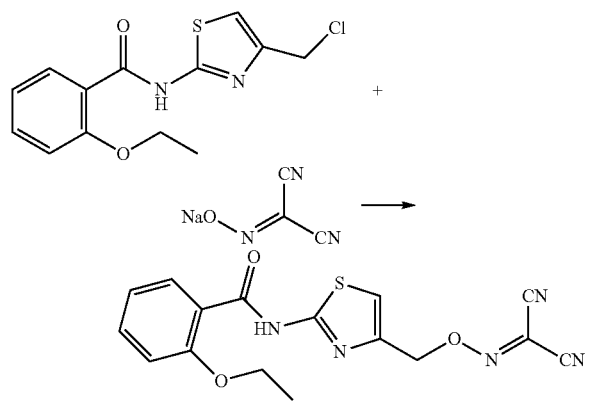

N-(4-(chloromethyl)thiazole-2-yl)-2-ethoxybenzamide (0.45 g, 1.52 mmol), sodium malononitrile oxime ether (0.18 g, 1.54 mmol) and 15 ml of acetonitrile were added to a 50 ml reaction flask, and heated to 60° C. to react while stirring; TLC (ethyl acetate:petroleum ether=1:3) monitoring was conducted; after the reaction was completed, the acetonitrile was evaporated off under reduced pressure; and the residue was purified by column chromatography (ethyl acetate:petroleum ether=1:3 as an eluent; 100-140-mesh silica gel produced by Qingdao Marine Biological Chemical Plant Branch) to obtain 0.25 g of yellow solid, with a yield of 46%.

According to the description of the above embodiments and the synthetic route of the general formula I in the summary of the present invention, other compounds shown by the general formula I can be obtained by replacing the raw materials.

Determination of Biological Activity

Embodiment 8

Determination of Control Effect on Plant Bacterial Diseases

The compounds of the present invention are used to determine the control effect on various plant bacterial diseases. For different bacterial diseases, the test procedures are as follows:

Melon bacterial fruit blotch: the compound to be tested is dissolved with a small amount of N,N dimethylformamide and diluted with water to the required concentration. The pathogenic bacteria cultured to a stable growth stage is evenly mixed with a quantitative compound solution; the germinated melon seeds are soaked in the mixed solution of a bacteria solution and the compound for half an hour; then, the seeds are sown in an earthworm soil culture cup and put into a greenhouse for moisturizing cultivation for two weeks generally; and the control effect is investigated after full onset of diseases through control.

Soft rot of Chinese cabbage: 2 cm of square Chinese cabbage leaf is cut and placed in a glass petri dish lined with double-layer filter paper. A compound dissolved in N,N dimethylformamide and diluted with water to a required concentration is sprayed onto the surface of the Chinese cabbage leaf. After the medicinal liquid on the surface of the Chinese cabbage leaf is dried in a fume hood, the surface of the Chinese cabbage leaf is acupunctured by using an inoculating needle to cause a wound. 5 ml of soft rot bacteria of Chinese cabbage cultured to a stable growth period is added to the wound for inoculation. Finally, the test materials are placed in an incubator and cultured for 48 hours in the dark; and the control effect is investigated after full onset of diseases through control.

Test results are as follows:

At 400 mg/L, compounds 4, 5, 6, 20, 22, 23, 34, 36, 45, 47, 65, 74, 86, 87, 95, 97, 99, 104, 117, 118, 119, 123, 134, 179, 228, 253, 361, 366 and 367 have 100% control effects on soft rot of Chinese cabbage.

At 400 mg/L, compounds 4, 5, 6, 20, 22, 23, 34, 36, 45, 47, 65, 74, 86, 87, 95, 97, 99, 104, 117, 118, 119, 123, 134, 179, 228, 253, 361, 366 and 367 have 100% control effects on melon bacterial fruit blotch.

Embodiment 9

Determination of Control Effect on Plant Fungal Diseases

An in vivo pot determination method was adopted, i.e., a sample of the compound to be tested was dissolved with a small amount of solvent (the type of the solvent may be, for example, acetone, methanol and DMF, and selected according to the capability to dissolve the sample; the volume ratio of the amount of the solvent to the amount of sprayed solution is equal to or less than 0.05), diluted with water containing 0.1% Tween 80 and formulated into a required concentration of solution to be tested. Foliar spray treatment was carried out with the compounds of the present invention at the designed concentrations. A blank control with clear water spray was set and repeated for three times. Disease inoculation was carried out on the second day after the treatment. After inoculation, the plants were placed in a phytotron for moisturizing cultivation (temperature: 25° C. on day, 20° C. at night, relative humidity 95-99%). After culturing the test material for 24 hours, the plants were transferred to a greenhouse for cultivation, and the plants that did not require moisturizing cultivation were directly inoculated and cultivated in the greenhouse. After the control was fully diseased (generally one week), the control effects of the compounds were evaluated. For the result survey, *A Manual of Assessment Keys for Plant Diseases* compiled by American Phytopathological Society can be referred to, which uses 100-0 for representation. "100" level represents no disease and "0" level represents the most severe disease degree.

Control effects on soybean rust:

For part of the test compounds, when the concentration of the following compounds is 400 ppm, compounds 10, 16, 19, 20, 22, 23, 34, 36, 47, 57, 65, 86, 87, 95, 98, 100, 117, 179, 363, 364 and 365 have better control effects on soybean rust, and the control effects are ≥80%.

According to the above method, compounds 10, 23, 47, 179 and 365 are selected for parallel comparison with the known compound CK1 in control of soybean rust. Test results are shown in Table 3.

TABLE 3

| Compound | Control Effects on Soybean Rust (%) | |
|---|---|---|
|  | 200 ppm | 100 ppm |
| 10 | 100 | 100 |
| 23 | 100 | 100 |
| 47 | 100 | 85 |
| 179 | 100 | 80 |
| 365 | 100 | 100 |
| CK1 | 0 | 0 |

Control effects on cucumber downy mildew:

For part of the test compounds, when the concentration of the following compounds is 400 ppm, compounds 10, 16, 19, 20, 22, 23, 36, 45, 47, 57, 65, 86, 87, 95, 97, 98, 100, 117, 123, 134, 179 and 365 have better control effects on cucumber downy mildew, and the control effects are ≥80%.

According to the above method, compounds 20, 45, 97 and 117 are selected for parallel comparison with the known compounds CK1, CK2 and CK3 in control of cucumber downy mildew. Test results are shown in Table 4.

TABLE 4

| Compound | Control Effects on Cucumber Downy Mildew (%) |
|---|---|
|  | 400 ppm |
| 20 | 100 |
| 45 | 100 |
| 97 | 100 |
| 117 | 100 |
| CK1 | 0 |
| CK2 | 0 |
| CK3 | 0 |

Embodiment 10

Field Trial

Compounds 47 and 97 were selected from the above compounds for field trial to control bacterial spot of cucumber (*Pseudomonas syringae* pv. *lachrymans*). The treatment dose of the test drug was 400 mg/L, and the treatment dose of a control drug CK2 was 700 mg/L. The test drug and the control drug were arranged in random blocks; the plot area was 15 m$^2$; and repetition was conducted for 3 times. The drug delivery mode was the whole plant spray. Drug delivery was conducted for three times, with an interval of 7 days, and control effect investigation was carried out 7 days after the last drug delivery. During investigation, 5 points in each plot were sampled; all leaves were investigated; and disease indexes and control effects were calculated according to the percentage level of diseased spot area of each leaf in the whole leaf area. Results are shown in Table 5.

TABLE 5

| Compound | Active Ingredient Dose (mg/L) | Control Effect (%) |
|---|---|---|
| 47 | 400 | 77.00 |
| 97 | 400 | 79.84 |
| CK2 | 700 | 76.89 |

The invention claimed is:

1. An oxime ether compound of formula I or a salt thereof:

wherein:

X is sulfur or oxygen;

Z is selected from hydrogen, and $C_1$-$C_6$ linear or branched alkyls that are unsubstituted or substituted with a substituent selected from halogen, cyano, trifluoromethyl, trifluoromethoxy, hydroxy, nitro, and amino;

A is CN, (C=O)OR$^1$, (C=O)NHR$^2$, or (C=O)NHNH$_2$;

R$^1$ is $C_1$-$C_8$ alkyl;

R$^2$ is hydrogen or $C_1$-$C_8$ alkyl;

W is selected from hydrogen, acetonitrile, $C_1$-$C_8$ alkyl, $C_1$-$C_8$ haloalkyl, $C_3$-$C_6$ cycloalkyl, $C_2$-$C_8$ alkenyl, $C_2$-$C_8$ haloalkenyl, $C_2$-$C_8$ alkynyl, $C_2$-$C_8$ haloalkynyl, $C_1$-$C_8$ alkoxy $C_1$-$C_8$alkyl, C(=O)R$^3$, C(=O)CH$_2$R$^3$, C(=O)CH$_2$OR$^3$, NO$_2$, OR$^4$, S(O)$_2$R$^5$, N(R$^6$)R$^7$, and N=C(R$^8$)R$^9$;

Q is selected from hydrogen, acetonitrile, $C_1$-$C_8$ alkyl, $C_1$-$C_8$ haloalkyl, $C_3$-$C_6$ cycloalkyl, $C_2$-$C_8$ alkenyl, $C_2$-$C_8$ haloalkenyl, $C_2$-$C_8$ alkynyl, $C_2$-$C_8$ haloalkynyl, $C_1$-$C_8$ alkoxy $C_1$-$C_8$ alkyl, and C(=O)R$^3$, or, Q, N and W are connected to N to form a 3-6 membered saturated or unsaturated ring that contains 0-2 heteroatoms selected from N—R$^{10}$, O, S, and oxidized S optionally substituted by R$^{11}$ or forms a fused ring with benzene ring;

R$^3$ is selected from hydrogen, $C_1$-$C_8$ alkyl, $C_1$-$C_8$ haloalkyl, $C_3$-$C_6$ cycloalkyl, $C_2$-$C_8$ alkenyl, $C_2$-$C_8$ haloalkenyl, $C_2$-$C_8$ alkynyl, $C_2$-$C_8$ haloalkynyl, $C_1$-$C_8$ alkoxy $C_1$-$C_8$ alkyl, N(R$^{12}$)R$^{13}$, optionally substituted aryl, and optionally substituted heteroaryl;

R$^4$ is selected from hydrogen, $C_1$-$C_8$ alkyl, $C_1$-$C_8$ haloalkyl, and $C_3$-$C_6$ cycloalkyl;

R$^5$ is selected from $C_1$-$C_2$ alkyl, $C_1$-$C_2$ haloalkyl, $C_3$-$C_6$ cycloalkyl, $C_1$-$C_4$ alkoxy, $C_1$-$C_4$ alkyl substituted phenyl, and N(R$^{12}$)R$^{13}$;

R$^6$ is hydrogen or $C_1$-$C_8$ alkyl;

R$^7$ is hydrogen or $C_1$-$C_8$ alkyl;

R$^8$ is selected from hydrogen, $C_1$-$C_8$alkyl, $C_1$-$C_8$ haloalkyl, and phenyl that is unsubstituted or optionally substituted by hydrogen, halogen, cyano, nitro, $C_1$-$C_4$ alkyl, or $C_1$-$C_4$ haloalkyl;

R$^9$ is selected from $C_1$-$C_8$ alkyl, $C_1$-$C_8$ haloalkyl, phenyl unsubstituted or optionally substituted by hydrogen, halogen, cyano, nitro, $C_1$-$C_4$ alkyl, or $C_1$-$C_4$ haloalkyl;

R$^{10}$ is selected from hydrogen, $C_1$-$C_2$ alkyl, $C_1$-$C_2$ haloalkyl, $C_1$-$C_2$ alkylcarbonyl, and $C_1$-$C_2$ alkoxycarbonyl;

$R^{11}$ is selected from H, halogen, CN, $NO_2$, $C_1$-$C_2$ alkyl, $C_1$-$C_2$ haloalkyl, $C_1$-$C_4$ alkoxy, $C_1$-$C_2$ haloalkoxy, optionally substituted aryl, and $S(O)nR^{14}$, wherein n is 0, 1 or 2;

$R^{12}$ is $C_1$-$C_8$ alkyl;

$R^{13}$ is $C_1$-$C_8$ alkyl; and $R^{14}$ is hydrogen, $C_1$-$C_2$ alkyl, $C_1$-$C_2$ haloalkyl, $C_3$-$C_6$ cycloalkyl, and $C_1$-$C_4$ alkoxy.

2. The oxime ether compound or the salt thereof according to claim 1, wherein in formula I:

X is sulfur or oxygen;

Z is selected from hydrogen, and $C_1$-$C_3$ linear or branched alkyl that are unsubstituted or substituted by halogen, cyano, trifluoromethyl, trifluoromethoxy, hydroxy, nitro, or amino;

A is CN, (C=O)$OR^1$, (C=O)$NHR^2$, or (C=O)$NHNH_2$;

$R^1$ is $C_1$-$C_4$ alkyl;

$R^2$ is hydrogen or $C_1$-$C_4$ alkyl;

W is selected from hydrogen, acetonitrile, $C_1$-$C_4$ alkyl, $C_1$-$C_4$ haloalkyl, $C_3$-$C_6$ cycloalkyl, $C_2$-$C_4$ alkenyl, $C_2$-$C_4$ haloalkenyl, $C_2$-$C_4$ alkynyl, $C_2$-$C_4$ haloalkynyl, $C_1$-$C_4$ alkoxy $C_1$-$C_4$ alkyl, C(=O)$R^3$, C(=O)$CH_2R^3$, C(=O)$CH_2OR^3$, $NO_2$, $OR^4$, $S(O)_2R^5$, $N(R^6)R^7$, and N=C($R^8$)$R^9$;

Q is selected from hydrogen, acetonitrile, $C_1$-$C_4$ alkyl, $C_1$-$C_4$ haloalkyl, $C_3$-$C_6$ cycloalkyl, $C_2$-$C_4$ alkenyl, $C_2$-$C_4$ haloalkenyl, $C_2$-$C_4$ alkynyl, $C_2$-$C_4$ haloalkynyl, $C_1$-$C_4$ alkoxy $C_1$-$C_4$ alkyl, and C(=O)$R^3$, or, Q, N and W are connected to N to form a 3-6 membered saturated or unsaturated ring comprising 0-2 heteroatoms selected from N—$R^{10}$, O, S and oxidized S, and optionally substituted by $R^{11}$ or forming a fused ring with benzene ring;

$R^3$ is selected from hydrogen, $C_1$-$C_4$ alkyl, $C_1$-$C_4$ haloalkyl, $C_3$-$C_6$ cycloalkyl, $C_2$-$C_4$ alkenyl, $C_2$-$C_4$ haloalkenyl, $C_2$-$C_4$ alkynyl, $C_2$-$C_4$ haloalkynyl, $C_1$-$C_4$ alkoxy $C_1$-$C_4$ alkyl, $N(R^{12})R^{13}$, unsubstituted or substituted phenyl, unsubstituted or substituted pyridyl, unsubstituted or substituted pyrazolyl, unsubstituted or substituted thiazolyl, unsubstituted or substituted isothiazolyl or unsubstituted or substituted thiadiazolyl, wherein the substituent is selected from hydrogen, halogen, cyano, nitro, hydroxyl, sulfhydryl, amino, aldehyde, C(=O)$NH_2$, $C_1$-$C_4$ alkyl, $C_1$-$C_4$ haloalkyl, $C_3$-$C_6$ cycloalkyl, $C_1$-$C_3$ alkoxy, $C_1$-$C_3$ haloalkoxy, $C_1$-$C_3$ alkylthio, $C_1$-$C_3$ haloalkylthio, $C_1$-$C_3$ alkylamino, $C_1$-$C_3$ dialkylamino, $C_3$-$C_6$ cycloalkylamino, $C_1$-$C_3$ alkoxycarbonyl, $C_1$-$C_3$ alkylsulfonyl, $C_1$-$C_3$ alkylaminocarbonyl, $C_1$-$C_3$ alkylaminosulfonyl, unsubstituted or substituted phenyl, and unsubstituted or substituted pyridyl, wherein the substituent for the substituted phenyl or substituted pyridyl is selected from hydrogen, halogen, cyano, nitro, $C_1$-$C_4$ alkyl, and $C_1$-$C_4$ haloalkyl;

$R^4$ is selected from hydrogen, $C_1$-$C_4$ alkyl, $C_1$-$C_4$ haloalkyl, and $C_3$-$C_6$ cycloalkyl;

$R^5$ is selected from $C_1$-$C_2$ alkyl, $C_1$-$C_2$ haloalkyl, $C_3$-$C_6$ cycloalkyl, $C_1$-$C_4$ alkoxy, $C_1$-$C_4$ alkyl substituted phenyl, and $N(R^{12})R^{13}$;

$R^6$ is selected from hydrogen or $C_1$-$C_4$ alkyl;

$R^7$ is hydrogen or $C_1$-$C_4$ alkyl;

$R^8$ is selected from hydrogen, $C_1$-$C_4$ alkyl, $C_1$-$C_4$ haloalkyl, and phenyl unsubstituted or optionally substituted with hydrogen, halogen, cyano, nitro;

$R^9$ is selected from $C_1$-$C_4$ alkyl, $C_1$-$C_4$ haloalkyl, and phenyl unsubstituted or optionally substituted with hydrogen, halogen, cyano, or nitro;

$R^{10}$ is selected from hydrogen, $C_1$-$C_2$ alkyl, $C_1$-$C_2$ haloalkyl, $C_1$-$C_2$ alkylcarbonyl, and $C_1$-$C_2$ alkoxycarbonyl;

$R^{11}$ is selected from H, halogen, CN, $NO_2$, $C_1$-$C_2$ alkyl, $C_1$-$C_2$ haloalkyl, $C_1$-$C_4$ alkoxy, $C_1$-$C_2$ haloalkoxy, optionally substituted aryl, and $S(O)nR^{14}$, wherein n is 0, 1 or 2;

$R^{12}$ is $C_1$-$C_4$ alkyl;

$R^{13}$ is $C_1$-$C_4$ alkyl; and $R^{14}$ is hydrogen, $C_1$-$C_2$ alkyl, $C_1$-$C_2$ haloalkyl, $C_3$-$C_6$ cycloalkyl or $C_1$-$C_4$ alkoxy.

3. The oxime ether compound or the salt thereof according to claim 2, wherein in formula I:

X is oxygen or sulfur;

Z is hydrogen, methyl, or ethyl;

A is CN, (C=O)$OR^1$, (C=O)$NHR^2$, or (C=O)$NHNH_2$;

$R^1$ is methyl or ethyl;

$R^2$ is hydrogen, methyl, or ethyl;

W is selected from hydrogen, $C_1$-$C_4$ alkyl, $C_1$-$C_4$ haloalkyl, $C_3$-$C_6$ cycloalkyl, C(=O)$R^3$, $OR^4$, $S(O)_2R^5$, $N(R^6)R^7$, and N=C($R^8$)$R^9$;

Q is selected from hydrogen, $C_1$-$C_4$ alkyl, $C_1$-$C_4$ haloalkyl, $C_3$-$C_6$ cycloalkyl, and C(=O)$R^3$, or, Q, N and W are connected to N to form a 3-6 membered saturated or unsaturated ring comprising 0-2 heteroatoms selected from N—$R^{10}$, O, S, and oxidized S; and optionally form a fused ring with the benzene ring;

$R^3$ is selected from $C_1$-$C_4$ alkyl, $C_1$-$C_4$ haloalkyl, $C_3$-$C_6$ cycloalkyl, $N(R^{12})R^{13}$, unsubstituted or substituted phenyl, unsubstituted or substituted pyridyl, unsubstituted or substituted pyrazolyl, unsubstituted or substituted thiazolyl, unsubstituted or substituted isothiazolyl, and unsubstituted or substituted thiadiazolyl, wherein the substituent is selected from of hydrogen, halogen, cyano, nitro, C(=O)$NH_2$, $C_1$-$C_4$ alkyl, $C_1$-$C_4$ haloalkyl, $C_3$-$C_6$ cycloalkyl, $C_1$-$C_3$ alkoxy, $C_1$-$C_3$ haloalkoxy, $C_1$-$C_3$ alkylthio, $C_1$-$C_3$ haloalkylthio, $C_1$-$C_3$ alkylamino, $C_1$-$C_3$ dialkylamino, $C_3$-$C_6$ cycloalkylamino, $C_1$-$C_3$ alkoxycarbonyl, $C_1$-$C_3$ alkylsulfonyl, $C_1$-$C_3$ alkylaminocarbonyl, $C_1$-$C_3$ alkylaminosulfonyl, unsubstituted or substituted phenyl, and unsubstituted or substituted pyridyl, wherein the substituent is selected from hydrogen, halogen, cyano, nitro, $C_1$-$C_4$ alkyl, and $C_1$-$C_4$ haloalkyl;

$R^4$ is hydrogen, $C_1$-$C_4$ alkyl, or $C_1$-$C_4$ haloalkyl;

$R^5$ is $C_1$-$C_2$ alkyl, $C_1$-$C_2$ haloalkyl, methyl substituted phenyl, or $N(R^{11})R^{12}$;

$R^6$ is hydrogen, methyl, or ethyl;

$R^7$ is hydrogen, methyl, or ethyl;

$R^8$ is selected from methyl, ethyl, trifluoromethyl, and phenyl that is unsubstituted or optionally substituted by hydrogen, halogen, cyano, or nitro;

$R^9$ is selected from methyl, ethyl, trifluoromethyl, and phenyl unsubstituted or optionally substituted by hydrogen, halogen, cyano, or nitro;

$R^{12}$ is methyl or ethyl; and $R^{13}$ is methyl or ethyl.

4. The oxime ether compound or the salt thereof according to claim 3, wherein in the general formula I:

X is oxygen or sulfur;

Z is hydrogen;

A is CN, (C=O)$OR^1$, or (C=O)$NH_2$;

$R^1$ is methyl or ethyl;

W is selected from hydrogen, $C_1$-$C_4$ alkyl, $C_1$-$C_4$ haloalkyl, $C_3$-$C_6$ cycloalkyl, C(=O)$R^3$, $S(O)_2R^5$, $N(R^6)R^7$, and N=C($R^8$)$R^9$;

Q is selected from hydrogen, $C_1$-$C_4$ alkyl, $C_1$-$C_4$ haloalkyl, $C_3$-$C_6$ cycloalkyl, and $C(=O)R^3$;

$R^3$ is selected from $C_1$-$C_4$ alkyl, $C_1$-$C_4$ haloalkyl, $C_3$-$C_6$ cycloalkyl, $N(R^{12})R^{13}$, unsubstituted or substituted phenyl, unsubstituted or substituted pyridyl, unsubstituted or substituted pyrazolyl, unsubstituted or substituted thiazolyl, unsubstituted or substituted isothiazolyl, and unsubstituted or substituted thiadiazolyl, wherein the substituent is selected from hydrogen, halogen, cyano, nitro, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, and $C_1$-$C_4$ haloalkylthio;

$R^5$ is $C_1$-$C_2$ alkyl, $C_1$-$C_2$ haloalkyl, p-methylphenyl, or $N(R^{12})R^{13}$;

$R^6$ is hydrogen, methyl, or ethyl;

$R^7$ is hydrogen, methyl, or ethyl;

$R^8$ is selected from methyl, ethyl, trifluoromethyl, and phenyl unsubstituted or optionally substituted by hydrogen, halogen, cyano, or nitro;

$R^9$ is selected from methyl, ethyl, trifluoromethyl, and phenyl unsubstituted or optionally substituted by hydrogen, halogen, cyano, or nitro;

$R^{12}$ is methyl or ethyl; and $R^{13}$ is methyl or ethyl.

5. The oxime ether compound or the salt thereof according to claim 4, wherein in formula I:

X is sulfur;

Z is hydrogen;

A is CN or $(C=O)NH_2$;

W is hydrogen, $C_1$-$C_4$ alkyl, $C_3$-$C_6$ cycloalkyl, $C(=O)R^3$, or $N=C(R^8)R^9$;

Q is hydrogen, $C_1$-$C_4$ alkyl, $C_3$-$C_6$ cycloalkyl, or $C(=O)R^3$;

$R^3$ is selected from $C_1$-$C_4$ alkyl, $C_1$-$C_4$ haloalkyl, $C_3$-$C_6$ cycloalkyl, unsubstituted or substituted phenyl, unsubstituted or substituted pyridyl, unsubstituted or substituted pyrazolyl, unsubstituted or substituted thiazolyl, unsubstituted or substituted isothiazolyl and unsubstituted or substituted thiadiazolyl, wherein the substituent is selected from hydrogen, halogen, cyano, nitro, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, and $C_1$-$C_4$ haloalkylthio;

$R^8$ is selected from methyl, ethyl, trifluoromethyl, and phenyl unsubstituted or optionally substituted by hydrogen, halogen, cyano, or nitro; and $R^9$ is selected from methyl, ethyl, trifluoromethyl, and phenyl unsubstituted or optionally substituted by hydrogen, halogen, cyano, or nitro.

6. The oxime ether compound or the salt thereof according to claim 5, wherein in formula I:

X is sulfur;

Z is hydrogen;

A is CN or $(C=O)NH_2$;

W is hydrogen, $C_1$-$C_4$ alkyl, or $C(=O)R^3$;

Q is hydrogen, $C_1$-$C_4$ alkyl, or $C(=O)R^3$;

$R^3$ is selected from $C_1$-$C_4$ alkyl, $C_1$-$C_4$ haloalkyl, $C_3$-$C_6$ cycloalkyl, group $K^1$ to group $K^{10}$, unsubstituted or substituted phenyl, and unsubstituted or substituted pyridyl, wherein the substituent is selected from halogen, cyano, nitro, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, and $C_1$-$C_4$ haloalkylthio;

group $K^1$ to group $K^{10}$ are

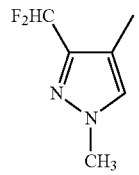 $K^1$

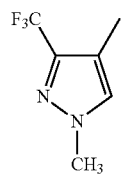 $K^2$

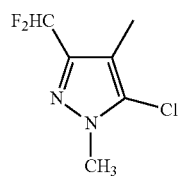 $K^3$

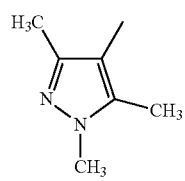 $K^4$

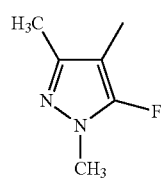 $K^5$

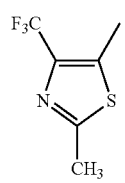 $K^6$

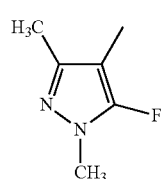 $K^7$

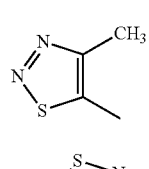 $K^8$

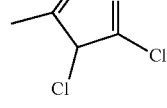 $K^9$

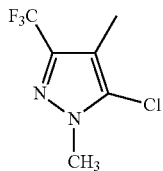 K10 wherein the salt is formed by reacting the compound of formula I and an acid selected from hydrochloric acid, hydrobromic acid, sulfuric acid, phosphoric acid, formic acid, acetic acid, propionic acid, butyric acid, pentanoic acid, trifluoroacetic acid, oxalic acid, malonic acid, methanesulfonic acid, 4-toluenesulfonic acid, malic acid, fumaric acid, lactic acid, maleic acid, salicylic acid, tartaric acid, and citric acid.

7. A method for controlling fungi and bacteria, comprising applying the oxime ether compound or the salt thereof according to claim 1 to a subject in need thereof.

8. A fungicidal and bactericidal composition, comprising the oxime ether compound or the salt thereof according to claim 1 as an active ingredient, wherein a weight percentage of the active ingredient in the composition is 0.1-99%.

9. A method for controlling plant diseases caused by bacteria or fungi, comprising applying an effective amount of the composition of claim 8 to a crop or a growth medium or site of the crop.

* * * * *